United States Patent
Imoto et al.

(10) Patent No.: US 10,799,156 B2
(45) Date of Patent: Oct. 13, 2020

(54) SHEET FOR IDENTIFICATION

(71) Applicant: NITTO DENKO CORPORATION, Ibaraki-shi, Osaka (JP)

(72) Inventors: Takashi Imoto, Ibaraki (JP); Akinori Nishio, Ibaraki (JP)

(73) Assignee: NITTO DENKO CORPORATION, Ibaraki-shi, Osaka (JP)

( * ) Notice: Subject to any disclaimer, the term of this patent is extended or adjusted under 35 U.S.C. 154(b) by 0 days.

(21) Appl. No.: 16/078,161

(22) PCT Filed: Nov. 29, 2016

(86) PCT No.: PCT/JP2016/085304
§ 371 (c)(1),
(2) Date: Aug. 21, 2018

(87) PCT Pub. No.: WO2017/145478
PCT Pub. Date: Aug. 31, 2017

(65) Prior Publication Data
US 2019/0046088 A1 Feb. 14, 2019

(30) Foreign Application Priority Data
Feb. 23, 2016 (JP) ................. 2016-032234

(51) Int. Cl.
*A61B 5/1172* (2016.01)
*C09J 7/20* (2018.01)
(Continued)

(52) U.S. Cl.
CPC ............ *A61B 5/1172* (2013.01); *C09J 7/20* (2018.01); *C09J 7/241* (2018.01); *C09J 7/255* (2018.01);
(Continued)

(58) Field of Classification Search
CPC ......... A61B 5/1172; C09J 7/385; C09J 7/241; C09J 7/255; C09J 7/38; C09J 7/20;
(Continued)

(56) References Cited

U.S. PATENT DOCUMENTS

| 4,221,404 A * | 9/1980 | Shuffstall ............... B42D 15/00 283/115 |
| 2012/0175424 A1* | 7/2012 | Saint ....................... G09F 3/005 235/492 |

FOREIGN PATENT DOCUMENTS

| JP | 11-301145 A | 11/1999 |
| JP | 2001-040299 A | 2/2001 |

(Continued)

OTHER PUBLICATIONS

International Search Report of PCT/JP2016/085304 dated Feb. 7, 2017.

*Primary Examiner* — Justin V Lewis
(74) *Attorney, Agent, or Firm* — Sughrue Mion, PLLC

(57) ABSTRACT

An identification sheet (X1) according to the present invention includes a backing sheet (10) and a pressure-sensitive adhesive sheet (20). The backing sheet (10) bears a distinguishing mark (M1). The pressure-sensitive adhesive sheet (20) has a multilayer structure including a substrate layer (21) and a pressure-sensitive adhesive layer (22). The pressure-sensitive adhesive layer (22) is removably attachable to the backing sheet (10). The pressure-sensitive adhesive sheet (20) bears a distinguishing mark (M2). The identification sheet (X1) as above is suitable for keeping on surely providing the admissibility of evidence of a collected target material to be identified.

14 Claims, 4 Drawing Sheets

(51) Int. Cl.
  *C09J 7/38* (2018.01)
  *C09J 7/24* (2018.01)
  *C09J 7/25* (2018.01)
(52) U.S. Cl.
  CPC .............. *C09J 7/38* (2018.01); *C09J 7/385* (2018.01); *C09J 2423/006* (2013.01); *C09J 2433/00* (2013.01); *C09J 2467/006* (2013.01); *C09J 2475/00* (2013.01)
(58) Field of Classification Search
  CPC .............. C09J 2475/00; C09J 2423/006; C09J 2433/00; C09J 2467/006
  USPC .................. 283/72, 74, 81, 94, 98, 100, 101
  See application file for complete search history.

(56) References Cited

FOREIGN PATENT DOCUMENTS

| | | |
|---|---|---|
| JP | 2003-089776 A | 3/2003 |
| JP | 2006-051763 A | 2/2006 |
| JP | 2007-181525 A | 7/2007 |
| JP | 2007-181526 A | 7/2007 |
| JP | 2007-182483 A | 7/2007 |
| JP | 2007-254619 A | 10/2007 |
| JP | 2010-169618 A | 8/2010 |

\* cited by examiner

[FIG. 1]

| Date (MM/DD/YY) | Collection number |
|---|---|
| | 0987654321 |

Case name

Collection place

Collected material

Witness _____ Seal

Collector _____ Seal

[FIG. 2]
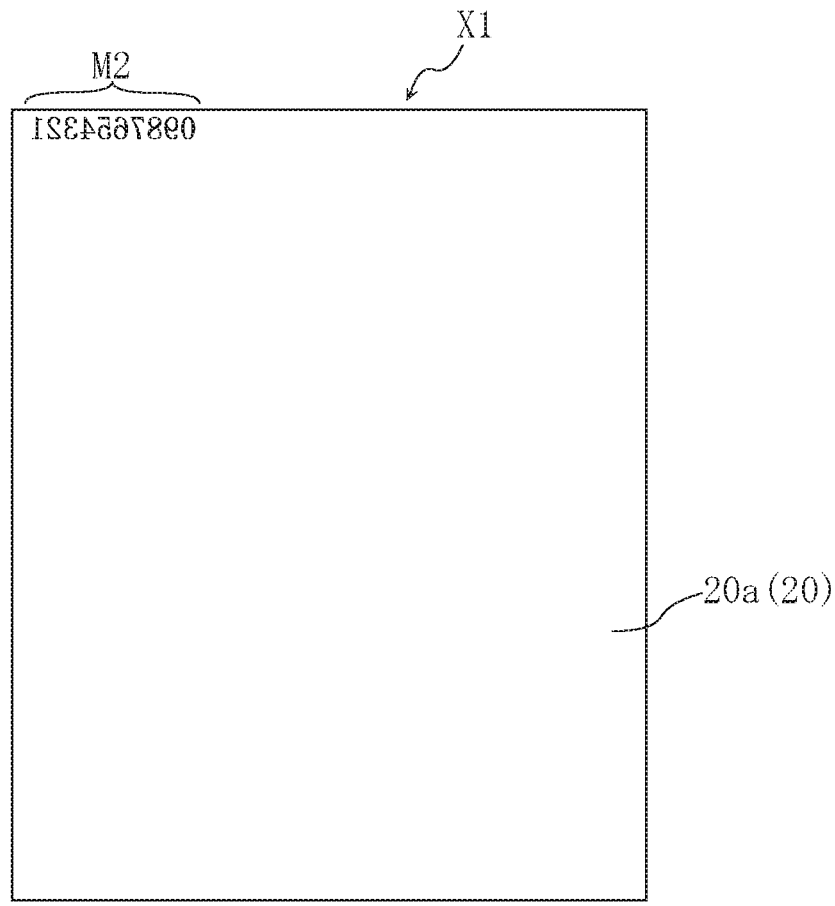
[FIG. 3]
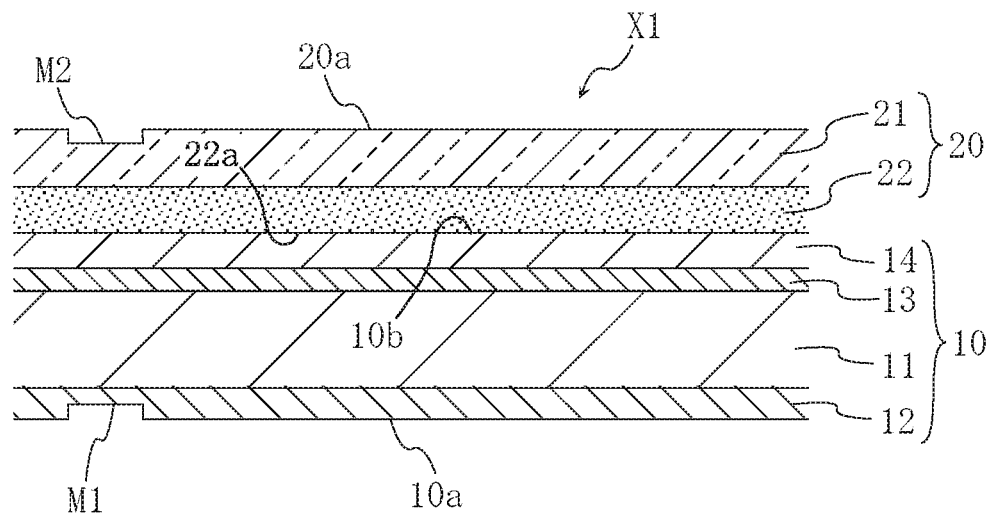

[FIG. 4]

| Date (MM/DD/YY) | Collection number 0987654321 |
|---|---|
| Case name | |
| Collection place | |
| Collected material | |
| Witness | Seal |
| Collector | Seal |
| 0987654324 | |

| Date (MM/DD/YY) | Collection number 0987654322 |
|---|---|
| Case name | |
| Collection place | |
| Collected material | |
| Witness | Seal |
| Collector | Seal |
| 0987654325 | |

| Date (MM/DD/YY) | Collection number 0987654323 |
|---|---|
| Case name | |
| Collection place | |
| Collected material | |
| Witness | Seal |
| Collector | Seal |
| 0987654326 | |

10a (10)

[FIG. 5]
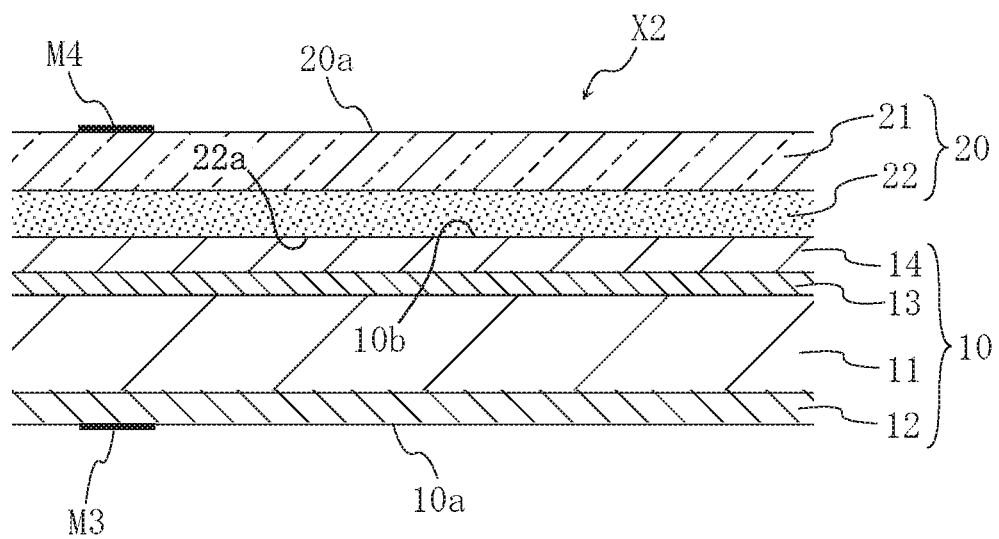

SHEET FOR IDENTIFICATION

CROSS REFERENCE TO RELATED APPLICATIONS

This application is a National Stage of International Application No. PCT/JP2016/085304 filed Nov. 29, 2016, claiming priority based on Japanese Patent Application No. 2016-032234 filed Feb. 23, 2016.

TECHNICAL FIELD

The present invention relates to sheets for identification (identification sheets) which are usable for collection and holding of materials to be identified (target materials).

BACKGROUND ART

Target materials to be identified, such as fingerprints and hairs, may be collected typically in a crime scene. For the collection, so-called identification sheets may be used. Such an identification sheet typically includes a mount sheet (backing sheet) and a transparent pressure-sensitive adhesive sheet, where the pressure-sensitive adhesive sheet has an adhesive face and is laminated onto the mount sheet. The mount sheet has a preprinted box in a surface on opposite side to the transparent pressure-sensitive adhesive sheet, where various information relating to the collection of a target material will be recorded in the box.

Using the identification sheet as above, a target material is collected typically by the following procedure. Initially, the transparent pressure-sensitive adhesive sheet is removed from the mount sheet to expose the adhesive face, and the target material is attached to the exposed adhesive face of the pressure-sensitive adhesive sheet. Of fingerprints left typically at a crime scene, latent fingerprints are invisible to the naked eye. Collection of such a latent fingerprint as the target material may be performed typically by the following procedure. Initially, a predetermined surface or region where the presence of the latent fingerprint is estimated is subjected to a treatment using a fine powder such as a fine aluminum powder. When the latent fingerprint is present in the region, the treatment allows the fine powder to be attached to the latent fingerprint to thereby visualize the pattern shape (including ridges) of the fingerprint. The transparent pressure-sensitive adhesive sheet is removed from the mount sheet to expose an adhesive face, and the exposed adhesive face is once pressed to, and then removed from, the region. Thus, the visualized fingerprint is transferred onto the adhesive face of the transparent pressure-sensitive adhesive sheet. The transparent pressure-sensitive adhesive sheet to which the target material, such as a fingerprint, is attached typically in the above manner is laminated again onto the original mount sheet. In the lamination, the adhesive face side, of the transparent pressure-sensitive adhesive sheet, bearing the target material is attached onto the mount sheet. To the box in the mount sheet, data relating to the collection of the target material, such as date, place, collected material name, and reference number, are recorded, and a person such as a collector signs and seals the mount sheet on its preprinted box. The information such as the data may be used to specify the target material, which is collected and held by the identification sheet, and will be information necessary for surely providing the admissibility of evidence when the target material is employed as evidence typically for a criminal case.

Identification sheets as above are described typically in Patent Literature (PTL) 1 to 4 as follows.

CITATION LIST

Patent Literature

PTL 1: Japanese Unexamined Patent Application Publication (JP-A) No. 2001-40299
PTL 2: JP-A No. 2003-89776
PTL 3: JP-A No. 2007-181525
PTL 4: JP-A No. 2007-181526

SUMMARY OF INVENTION

Technical Problem

It is important for a target material, which is collected and held by an identification sheet, to surely have the admissibility of evidence required when the target material is used as evidence typically for a criminal case. However, assume that the transparent pressure-sensitive adhesive sheet, which bears the true target material on the adhesive face and adheres to the mount sheet, is replaced with another transparent pressure-sensitive adhesive sheet bearing another target material. In this case, the other target material is, objectively and actually, not one that is specified typically by the various information recorded on the mount sheet. Also assume that the mount sheet, to which the transparent pressure-sensitive adhesive sheet bearing the true target material is attached and on which data such as various information for the target material are recorded, is replaced with another mount sheet on which other data such as various information are written. In this case, the data such as the information recorded on the other mount sheet is, objectively and actually, not one that specifies the target material borne by the pressure-sensitive adhesive sheet. These objective, actual inconsistencies between the target material adhering to the transparent pressure-sensitive adhesive sheet and the information to specify the target material recorded on the mount sheet may impair the value of evidence and may consequently impair the admissibility of evidence when the target material is used as evidence typically for a criminal case. The objective, actual inconsistencies between the target material and the data, such as the specifying information, on the mount sheet in the identification sheet may occur as a result of a tampering act on the identification sheet that holds the target material, or as a result of mistaking of a transparent pressure-sensitive adhesive sheet or a mount sheet for another during a process to collect the target material (collecting process) and during an operation to identify the target material (identifying operation).

The present invention has been made on the basis of these circumstances and has an object to provide an identification sheet that is suitable for keeping on surely providing the admissibility of evidence of a collected target material.

Solution to Problem

The present invention provides, in a first aspect, an identification sheet which includes a backing sheet and a pressure-sensitive adhesive sheet. The backing sheet bears a first distinguishing mark. The pressure-sensitive adhesive sheet has a multilayer structure including a pressure-sensitive adhesive layer and a substrate layer. The pressure-sensitive adhesive layer is removably attachable to the backing sheet. The pressure-sensitive adhesive sheet bears a second distinguishing mark.

The identification sheet according to the aspect includes the backing sheet (mount sheet; support sheet) and the pressure-sensitive adhesive sheet, which are removable or separable from each other. The backing sheet bears the first distinguishing mark, which is usable as first distinguishing information. The pressure-sensitive adhesive sheet bears the second distinguishing mark, which is usable as second distinguishing information. The first and second distinguishing marks can be configured to function as a pair of cross-check information so as to determine whether a backing sheet with the first distinguishing mark and a pressure-sensitive adhesive sheet with the second distinguishing mark correspond to each other, by designing the two distinguishing marks to correspond to each other. The first and second distinguishing marks that function as a pair of cross-check information may have pattern shapes that are identical to or different from each other. The first and second distinguishing marks may include at least one selected typically from numeric characters, alphabetic characters, hiragana characters, katakana characters, kanji characters, symbols, bar codes, and QR Codes. Examples of the bar codes include one-dimensional bar codes and two-dimensional bar codes.

Using the identification sheet having the configuration as above, a target material (material to be identified) may be collected typically by the following procedure. The pressure-sensitive adhesive sheet with the second distinguishing mark is removed from the backing sheet with the first distinguishing mark, and the target material is then attached to the exposed pressure-sensitive adhesive layer or the adhesive face of the pressure-sensitive adhesive sheet. The pressure-sensitive adhesive sheet with the second distinguishing mark, which bears the target material, is laminated again onto the original backing sheet with the first distinguishing mark. In the lamination, the adhesive face side, of the transparent pressure-sensitive adhesive sheet, bearing the target material is attached onto the backing sheet. On a writable surface, which may be provided in a predetermined area of the backing sheet, data relating to the collection of the target material are recorded (written), and a person such as a collector signs and seals the backing sheet on its writable surface. Non-limiting examples of the data include date, place, collected material name, and reference number. In the identification sheet, which is used typically in the above manner, the first distinguishing mark of the backing sheet and the second distinguishing mark of the pressure-sensitive adhesive sheet correspond to each other and act as a pair in the single identification sheet. This guarantees that the backing sheet and the pressure-sensitive adhesive sheet correspond to each other. Assume that, in the identification sheet after the collection of the target material, the pressure-sensitive adhesive sheet bearing the true target material and adhering to the backing sheet is removed and replaced with another pressure-sensitive adhesive sheet, where the other pressure-sensitive adhesive sheet is a pressure-sensitive adhesive sheet that lacks the second distinguishing mark corresponding to the first distinguishing mark of the backing sheet. In this case, there can be determined the absence of mutual correspondence between the backing sheet and the pressure-sensitive adhesive sheet after replacement (the other pressure-sensitive adhesive sheet). This is because the other pressure-sensitive adhesive sheet lacks the second distinguishing mark corresponding to the first distinguishing mark of the backing sheet. Assume that, in the identification sheet after the collection of the target material, the backing sheet, to which the pressure-sensitive adhesive sheet bearing the true target material adheres and on which the data such as various information for the target material are recorded, is removed and replaced with another backing sheet, where the other backing sheet is a backing sheet that lacks the first distinguishing mark corresponding to the second distinguishing mark of the pressure-sensitive adhesive sheet. In this case, there can be determined the lack of mutual correspondence between the pressure-sensitive adhesive sheet and the backing sheet after replacement (the other backing sheet). This is because the other backing sheet lacks the first distinguishing mark corresponding to the second distinguishing mark of the pressure-sensitive adhesive sheet. Namely, if the identification sheet undergoes such a replacement, the replacement can be detected or recognized. This is because the identification sheet includes the backing sheet and the pressure-sensitive adhesive sheet, where the backing sheet bears the first distinguishing mark, which is one of a pair of cross-check information, and the pressure-sensitive adhesive sheet bears the second distinguishing mark, which is the other of the pair of cross-check information. The identification sheet as above is suitable for restraining a tampering act on the identification sheet after the collection of the target material and for restraining the mistaking of the pressure-sensitive adhesive sheet or the backing sheet for another one during a collecting process and an identifying operation for the target material. Consequently, the identification sheet is suitable for surely providing the admissibility of evidence required of the target material collected typically in a criminal case.

In addition, in the identification sheet, the first distinguishing mark has been formed at the backing sheet, separately from the second distinguishing mark; and the second distinguishing mark has been formed at the pressure-sensitive adhesive sheet, separately from the first distinguishing mark. In the backing sheet, the first distinguishing mark may be made at the mount face to which the pressure-sensitive adhesive sheet adheres, or at an outer face on opposite side to the mount face, or in the interior of the backing sheet. To provide the first distinguishing mark in the interior of the backing sheet, for example, a sheet having a multilayer structure is employed as the backing sheet, and the first distinguishing mark is made at a predetermined face during the process of forming and stacking layers to constitute the backing sheet, so that the predetermined face is positioned in the interior of the multilayer structure. In the pressure-sensitive adhesive sheet, the second distinguishing mark may be made at a surface of the transparent substrate layer, where the surface faces the pressure-sensitive adhesive layer, or at an outer face in the substrate layer on opposite side to the pressure-sensitive adhesive layer, or in the interior of the substrate layer. To provide the second distinguishing mark in the interior of the substrate layer, for example, a multilayer assembly having a multilayer structure is employed as the substrate layer, and the second distinguishing mark is made at a predetermined face during the formation and stacking of layers to constitute the substrate layer, so that the predetermined face is positioned in the interior of the multilayer structure. The first distinguishing mark in the identification sheet is neither one formed by copying as a result of a transferring action of a coloring component constituting part of another distinguishing mark; nor one formed by copying as a result of a physical and/or chemical reaction caused typically by local heating, pressurization, or photoirradiation in the formation of another distinguishing mark. The second distinguishing mark in the identification sheet is neither one formed by copying as a result of a transferring action of a coloring component constituting part of another distinguishing mark; nor one formed by copying as a result of a physical and/or chemical reaction caused typically by local heating, pressurization, or photoirradiation in the formation of another distinguishing mark. The first and second distinguishing marks are ones separately or individually formed or engraved in the identification sheet. This configuration is advantageous for restraining or avoiding deterioration of the first and second distinguishing marks and is therefore suitable for allowing the two distinguishing marks to keep on functioning as a pair of cross-check information so as to determine the mutual correspondence between a backing sheet with the first distinguishing mark and a pressure-sensitive adhesive sheet with the second distinguishing mark.

As described above, the identification sheet is suitable for restraining a tampering act on the identification sheet after the collection of the target material and for restraining mistaking of the pressure-sensitive adhesive sheet or the backing sheet for another one during a collecting process and an identifying operation for the target material. Consequently, the identification sheet is suitable for keeping on surely providing the admissibility of evidence of the collected target material, where the admissibility of evidence is required typically in a criminal case.

The present invention also provides, in a second aspect, an identification sheet which includes a backing sheet and a pressure-sensitive adhesive sheet. The backing sheet has a first outer face and a mount face. The first outer face bears a first distinguishing mark. The mount face is disposed on opposite side to the first outer face. The pressure-sensitive adhesive sheet has a multilayer structure including a pressure-sensitive adhesive layer and a substrate layer. The pressure-sensitive adhesive layer is removably attachable to the mount face of the backing sheet. The pressure-sensitive adhesive sheet has a second outer face in the substrate layer, where the second outer face is on opposite side to the pressure-sensitive adhesive layer and bears a second distinguishing mark.

The identification sheet according to this aspect includes the backing sheet and the pressure-sensitive adhesive sheet, which are removable or separable from each other. The identification sheet has the first outer face in the backing sheet, where the first outer face may define one of outer surfaces of the identification sheet; and has the second outer face in the pressure-sensitive adhesive sheet, where the second outer face may define the other outer surface. The first outer face in the backing sheet bears the first distinguishing mark, which is usable as first distinguishing information. The first outer face bearing the first distinguishing mark may be covered with a transparent protective film. The second outer face in the pressure-sensitive adhesive sheet bears the second distinguishing mark, which is usable as second distinguishing information. The second outer face bearing the second distinguishing mark may be covered with a transparent protective film. The first and second distinguishing marks in the identification sheet can be configured to function as a pair of cross-check information to determine whether a backing sheet with the first distinguishing mark and a pressure-sensitive adhesive sheet with the second distinguishing mark correspond to each other, by designing the two distinguishing marks to correspond to each other. The first and second distinguishing marks that function as a pair of cross-check information may have pattern shapes identical to or different from each other. The first and second distinguishing marks each independently include at least one selected typically from numeric characters, alphabetic characters, hiragana characters, katakana characters, kanji characters, symbols, bar codes, and QR Codes. Examples of the bar codes include one-dimensional bar codes and two-dimensional bar codes.

Using the identification sheet having the configuration as above, a target material (material to be identified) may be collected typically by the following procedure. The pressure-sensitive adhesive sheet having the second outer face with the second distinguishing mark is removed from the mount face of the backing sheet having the first outer face with the first distinguishing mark. The target material is then attached to the exposed pressure-sensitive adhesive layer or the adhesive face of the pressure-sensitive adhesive sheet. The pressure-sensitive adhesive sheet with the second distinguishing mark, which bears the target material, is laminated again onto the mount face of the original backing sheet with the first distinguishing mark. In the lamination, the adhesive face side, of the transparent pressure-sensitive adhesive sheet, bearing the target material is attached onto the mount face. On a writable surface, which may be provided in a predetermined area of the backing sheet, data relating to the collection of the target material are recorded or written, and a person such as a collector signs and seals the backing sheet on its writable surface. Non-limiting examples of the data include date, place, collected material name, and reference number. In the identification sheet, which is used typically in the above manner, the first distinguishing mark of the backing sheet and the second distinguishing mark of the pressure-sensitive adhesive sheet correspond to each other and act as a pair in the single identification sheet. This guarantees that the backing sheet and the pressure-sensitive adhesive sheet correspond to each other. Assume that, in the identification sheet after the collection of the target material, the pressure-sensitive adhesive sheet bearing the true target material and adhering to the backing sheet is removed and replaced with another pressure-sensitive adhesive sheet, where the other pressure-sensitive adhesive sheet is a pressure-sensitive adhesive sheet that lacks the second distinguishing mark corresponding to the first distinguishing mark of the backing sheet. In this case, there can be determined the absence of mutual correspondence between the backing sheet and the pressure-sensitive adhesive sheet after replacement (the other pressure-sensitive adhesive sheet). This is because the other pressure-sensitive adhesive sheet lacks the second distinguishing mark corresponding to the first distinguishing mark of the backing sheet. Assume that, in the identification sheet after the collection of the target material, the backing sheet, to which the pressure-sensitive adhesive sheet bearing the true target material adheres, and on which the data such as various information for the target material are recorded, is removed and replaced with another backing sheet, where the other backing sheet is a backing sheet that lacks the first distinguishing mark corresponding to the second distinguishing mark of the pressure-sensitive adhesive sheet. In this case, there can be determined the absence of mutual correspondence between the pressure-sensitive adhesive sheet and the backing sheet after replacement (the other backing sheet). This is because the other backing sheet lacks the first distinguishing mark corresponding to the second distinguishing mark of the pressure-sensitive adhesive sheet. Specifically, the identification sheet includes the backing sheet and the pressure-sensitive adhesive sheet, where the backing sheet bears the first distinguishing mark, which is one of the pair of cross-check information, and the pressure-sensitive adhesive sheet bears the second distinguishing mark, which is the other of the pair of cross-check information. If the identification sheet undergoes such a replacement as above, the replacement can be detected or recognized. The identification sheet is therefore suitable for restraining a tampering act on the identification sheet after the collection of the target material and for restraining the mistaking of the pressure-sensitive adhesive sheet or the backing sheet for another one during a collecting process and an identifying operation for the target material. Consequently, the identification sheet is suitable for surely providing the admissibility of evidence required of the target material collected typically in a criminal case.

In addition, in the identification sheet, the first distinguishing mark has been formed at the first outer face of the backing sheet, separately from the second distinguishing mark; and the second distinguishing mark has been formed at the second outer face of the pressure-sensitive adhesive sheet, separately from the first distinguishing mark. The first distinguishing mark in the identification sheet is neither one formed by copying as a result of a transferring action of a coloring component constituting part of another distinguishing mark; nor one formed by copying as a result of a physical and/or chemical reaction caused typically by local heating, pressurization, or photoirradiation in the formation of another distinguishing mark. The second distinguishing mark in the identification sheet is neither one formed by copying as a result of a transferring action of a coloring component constituting part of another distinguishing mark; nor one formed by copying as a result of a physical and/or chemical reaction caused typically by local heating, pressurization, or photoirradiation in the formation of another distinguishing mark. The first and second distinguishing marks are ones separately or individually formed or engraved in the identification sheet. This configuration is advantageous for restraining or avoiding deterioration of the first and second distinguishing marks and is therefore suitable for allowing the two distinguishing marks to keep on functioning as a pair of cross-check information so as to determine the mutual correspondence between a backing sheet with the first distinguishing mark and a pressure-sensitive adhesive sheet with the second distinguishing mark.

As described above, the identification sheet is suitable for restraining a tampering act on the identification sheet after the collection of the target material and for restraining mistaking of the pressure-sensitive adhesive sheet or the backing sheet for another one during a collecting process and an identifying operation for the target material. Consequently, the identification sheet is suitable for keeping on surely providing the admissibility of evidence of the collected target material, where the admissibility of evidence is required typically in a criminal case.

Preferably, the first distinguishing mark and the second distinguishing mark are each independently selected from an engraved mark and a printed mark. As used herein, the term "engraved mark" refers to a mark which is made by engraving to form a concave in a face to be marked. Non-limiting examples of the engraving technique include laser marking and marking with air pen (air pen marking). More preferably, the first distinguishing mark and the second distinguishing mark are each independently selected from a laser mark, which is an engraved mark formed by laser marking; and a mark resulting from air pen marking, which is an engraved mark formed by air pen marking. These configurations are suitable for restraining or avoiding deterioration of the first and second distinguishing marks. The configurations are therefore advantageous for allowing the two distinguishing marks to keep on functioning as a pair of cross-check information to determine the mutual correspondence between a backing sheet with the first distinguishing mark and a pressure-sensitive adhesive sheet with the second distinguishing mark. Such an engraved mark is advantageous for giving a face to be marked, which less undergoes a shape change (such as formation of scratch marks) other than the formed distinguishing mark. In addition, the laser mark, which is a mark formed by laser marking, is also advantageous in that the pattern shape of the distinguishing mark can be designed or determined with high degree of freedom. This contributes to better productivity of the identification sheet.

The engraved mark formed by laser marking is also advantageous for surely providing removability or releasability between the backing sheet and the pressure-sensitive adhesive sheet. Assume that, in an identification sheet including a backing sheet and a pressure-sensitive adhesive sheet laminated on each other, a laser mark is formed as a through hole penetrating the backing sheet by laser irradiation from the backing sheet side, or a laser mark is formed as a through hole penetrating the pressure-sensitive adhesive sheet by laser irradiation from the pressure-sensitive adhesive sheet side, or a laser mark is formed as a through hole penetrating the entire identification sheet by laser irradiation. In these cases, the pressure-sensitive adhesive is softened and melted at or around an area, in which the through hole is formed, in a surface of the pressure-sensitive adhesive layer of the pressure-sensitive adhesive sheet, where the surface faces the backing sheet. Thus, the pressure-sensitive adhesive layer is liable to fuse to the backing sheet in the area. The fusion, if occurring, may impede the separation, namely, the removal between the backing sheet and the pressure-sensitive adhesive sheet, and/or may cause the pressure-sensitive adhesive layer to be significantly damaged, because the pressure-sensitive adhesive layer at the fused portion is pulled by the backing sheet upon removal (separation). In the configuration, the identification sheet includes an engraved mark formed by laser marking as at least one of the first distinguishing mark and the second distinguishing mark. This configuration is advantageous for avoiding or minimizing the occurrence of local fusion between the backing sheet and the pressure-sensitive adhesive sheet, and for surely providing the removability between the two sheets. Softening and melting of the pressure-sensitive adhesive in the adhesive face causes deformation of the softened-melted portion in the pressure-sensitive adhesive layer. The resulting deformation or unevenness in the adhesive face tends to lower the adhesion between the backing sheet and the pressure-sensitive adhesive sheet, when the two sheets after removal are laminated again on each other. The configuration, where the identification sheet includes the engraved mark formed by laser marking as at least one of the first distinguishing mark and the second distinguishing mark, is advantageous for avoiding or minimizing such deformation and unevenness in the adhesive face, and for surely providing the adhesion between the backing sheet and the pressure-sensitive adhesive sheet after re-lamination.

Preferably, the substrate layer of the pressure-sensitive adhesive sheet includes one selected from a polyethylene terephthalate film and a polyolefin film. Preferably, the substrate layer has a thickness of 2.5 to 500 μm. These configurations are advantageous for allowing the substrate layer to function as a carrier (support) in the pressure-sensitive adhesive sheet.

Preferably, the pressure-sensitive adhesive layer includes a polyurethane as a principal component (base polymer).

Such a polyurethane has urethane bonds, which are hydrogen-bonding functional groups each containing both a hydrogen donor group and a hydrogen acceptor group. The polyurethane containing the functional groups as above can form hydrogen bonds between its molecular chains to undergo cohesion, and has relatively high cohesive energy. The polyurethane therefore tends to actually provide a high softening temperature and/or a high glass transition temperature, namely, high thermal stability. The configuration, where such a polyurethane is contained as a principal component in the pressure-sensitive adhesive layer, readily actually provides high thermal stability and/or low fluidity (flowability) in the pressure-sensitive adhesive layer of the identification sheet. The high thermal stability and/or low fluidity of the pressure-sensitive adhesive layer in the identification sheet contributes to long-term, stable storage of the target material held by the identification sheet. Assume that heat transfer to the pressure-sensitive adhesive layer and/or heat evolution in the pressure-sensitive adhesive layer occurs during marking of a distinguishing mark in a process of identification sheet production. In this case, the high thermal stability or high heat resistance of the pressure-sensitive adhesive layer in the identification sheet also contributes to eliminating or minimizing deformation and failure, due to the heat, of the pressure-sensitive adhesive layer. The polyurethane or the pressure-sensitive adhesive contained in the pressure-sensitive adhesive layer in the identification sheet has a softening temperature of preferably 190° C. to 280° C. The softening temperature of the pressure-sensitive adhesive may be measured typically using a thermomechanical analyzer TMA/SS7100 (trade name, supplied by SII NanoTechnology Inc.). In the measurement, for example, a test piece (6 mm by 6 mm) to be subjected to the measurement is cut out from a sample pressure-sensitive adhesive sheet having a multilayer structure including a polyethylene terephthalate substrate and a pressure-sensitive adhesive layer (thickness: 290 µm). This measurement is performed in a penetration mode using a needle penetrator probe having a tip diameter of 1 mm under a load of 1470 mN, in which the tip of the probe is brought in contact with the central part of the pressure-sensitive adhesive surface of the test piece. In the measurement, the temperature is raised from a start temperature of 150° C. up to an end temperature of 320° C. at a rate of temperature rise of 10° C./min, in a nitrogen stream at a flow rate of 200 ml/min. The glass transition temperature of the pressure-sensitive adhesive may be measured by differential scanning calorimetry (DSC) in conformity to Japanese Industrial Standards (JIS) K 7121: Testing Methods for Transition Temperatures of Plastics.

The polyurethane, when contained in the pressure-sensitive adhesive layer, is preferably a polyester polyurethane. Such a polyester polyurethane has ester bonds, which are hydrogen acceptor groups, in addition to urethane bonds as described above. In the polyester polyurethane, the ester bonds less cause molecular chains to cohere with each other, as compared with the urethane bonds. The regulation of the content or proportion of ester bonds in the polyester polyurethane can be used as one of approaches to control the cohesiveness of the polyester polyurethane. Accordingly, the polyester polyurethane, which contains the ester bonds in addition to the urethane bonds, is easily controllable on the cohesive force between its molecular chains, within such a range as to give high thermal stability. In addition, the polyester polyurethane can be formed from material monomers selectable from among a wide variety of practically easily available high-purity monomers. With increasing purities of material monomers, a polymer resulting from the material monomers tends to have higher transparency. Accordingly, such a polyester polyurethane, which can be formed from material monomers selectable from among a wide variety of practically easily available high-purity monomers, tends to actually have high transparency. The configuration, where the polyester polyurethane is contained as a principal component in the pressure-sensitive adhesive layer, allows the pressure-sensitive adhesive layer in the identification sheet to surely have high thermal stability and/or low fluidity, to still be readily controllable on cohesiveness, and to actually have high transparency. The high thermal stability and/or low fluidity of the pressure-sensitive adhesive layer in the identification sheet contributes to long-term, stable storage of the target material held by the identification sheet. Assume that heat transfer to the pressure-sensitive adhesive layer and/or heat evolution in the pressure-sensitive adhesive layer occurs during marking of a distinguishing mark in a process of identification sheet production. In this case, the high thermal stability or high heat resistance of the pressure-sensitive adhesive layer in the identification sheet also contributes to eliminating or minimizing deformation and failure, due to the heat, of the pressure-sensitive adhesive layer. Control of the cohesiveness of the pressure-sensitive adhesive layer contributes to allowing the pressure-sensitive adhesive layer to actually have good adhesive strength and to less leave adhesive residue on an adherend after the pressure-sensitive adhesive sheet or the pressure-sensitive adhesive layer is removed from the adherend. Assume that laser marking is employed to form the distinguishing marks in the process of identification sheet production. In this case, the high transparency of the pressure-sensitive adhesive layer in the identification sheet contributes to restraining heat evolution in the pressure-sensitive adhesive layer due to laser beam absorption and contributes to eliminating or minimizing thermal deformation and thermal failure of the pressure-sensitive adhesive layer.

The polyester polyurethane, when contained in the pressure-sensitive adhesive layer, preferably includes units derived from a multifunctional isocyanate, units derived from a polycarboxylic acid, and units derived from a first polyhydric alcohol. This configuration can appropriately give the polyester polyurethane with the technical effects.

The polyester polyurethane in the pressure-sensitive adhesive layer is preferably a polyester-polyether polyurethane. The polyester-polyether polyurethane contains a polyether skeleton in addition to urethane bonds and ester bonds as described above. Ether bonds contained in the polyether skeleton have low optical absorptivity and are more flexible or movable as compared with carbon-carbon-carbon bonds. The polyester-polyether polyurethane, which contains such a polyether skeleton in addition to urethane bonds and ester bonds, tends to actually have high transparency and good flexibility while controlling the cohesive force between molecular chains within such a range as to give high thermal stability. Polyester polyurethanes, to which the polyester-polyether polyurethane belongs, can be formed from material monomers which are selectable from among a wide variety of practically easily available high-purity monomers. Accordingly, the polyester-polyether polyurethane, which belongs to polyester polyurethanes obtainable from material monomers which can be selectable from among a wide variety of easily available high-purity monomers, is liable to actually have high transparency. The configuration, where a polyester-polyether polyurethane is contained as a principal component in the pressure-sensitive adhesive layer, tends to allow the pressure-sensitive adhesive layer in the identification sheet to have high thermal stability and/or low fluidity, to have readily controllable cohesiveness, and to still actually have both high transparency and good flexibility. The high thermal stability and/or the low fluidity of the pressure-sensitive adhesive layer in the identification sheet contributes to long-term, stable storage of the target material held by the identification sheet. Assume that heat transfer to the pressure-sensitive adhesive layer and/or heat evolution in the pressure-sensitive adhesive layer occurs during marking of a distinguishing mark in a process of identification sheet production. In this case, the high thermal stability or heat resistance of the pressure-sensitive adhesive layer in the identification sheet also contributes to eliminating or minimizing deformation and failure, due to the heat, of the pressure-sensitive adhesive layer. Control of cohesiveness of the pressure-sensitive adhesive layer contributes to allowing the pressure-sensitive adhesive layer to actually have good adhesive strength and to less leave adhesive residue on an adherend after the pressure-sensitive adhesive sheet or the pressure-sensitive adhesive layer is removed from the adherend. Assume that a distinguishing mark is formed by laser marking in the process of identification sheet production. In this case, the high transparency of the pressure-sensitive adhesive layer in the identification sheet contributes to restraining heat evolution in the pressure-sensitive adhesive layer due to laser beam absorption and contributes to eliminating or minimizing thermal deformation and thermal failure of the pressure-sensitive adhesive layer. With increasing flexibility of the pressure-sensitive adhesive layer in the identification sheet, the adhesive face or the pressure-sensitive adhesive layer more readily conforms typically to, and deforms with, the surface asperities of a target material when the adhesive face of the pressure-sensitive adhesive layer is pressed onto the target material, and the surface asperities of the target material is more readily transferred onto the pressure-sensitive adhesive layer. Balancing between flexibility and thermal stability-low fluidity of the pressure-sensitive adhesive layer in the identification sheet can allow the pressure-sensitive adhesive layer or the adhesive face to actually have such tackiness as to adhere to the target material with good conformity to the asperities and can still restrain so-called stringiness of the pressure-sensitive adhesive between an adherend and the adhesive face upon removal of the pressure-sensitive adhesive layer from the adherend.

The polyester-polyether polyurethane, when contained in the pressure-sensitive adhesive layer, preferably includes units derived from a multifunctional isocyanate, units derived from a polycarboxylic acid, units derived from a first polyhydric alcohol, and units derived from a second polyhydric alcohol containing an ether bond. This configuration can appropriately give the polyester-polyether polyurethane with the technical effects.

In the polyester polyurethane in the pressure-sensitive adhesive layer, a ratio is preferably 0.5 to 1.5, more preferably 0.7 to 1.4, furthermore preferably 0.7 to 1.3, and still more preferably 0.8 to 1.2, where the ratio is the ratio of the total number of hydroxy groups assigned to polyhydric alcohol-derived units (namely, the total number of hydroxy groups of a polyhydric alcohol to form the polyhydric alcohol-derived units) to the sum of the total number of isocyanate groups assigned to multifunctional isocyanate-derived units (namely, the total number of isocyanate groups of a multifunctional isocyanate to constitute the multifunctional isocyanate-derived units) and the total number of carboxy groups assigned to polycarboxylic acid-derived units (namely, the total number of carboxy groups of a polycarboxylic acid to form the polycarboxylic acid-derived units). With the ratio approaching 1, the polyester polyurethane tends to have a higher molecular weight and, due to such a high molecular weight, tends to have higher cohesiveness between molecules of the polyester polyurethane. With the ratio decreasing less than 1, isocyanate groups and carboxy groups tend to be present in a total number larger than the number of hydroxy groups in entire molecular ends of the polyester polyurethane, and, accordingly, the cohesiveness between molecules of the polyester polyurethane tends to be higher, where the cohesiveness is due to the presence of isocyanate groups and carboxy groups, both of which are highly polar groups which relatively highly polarize. With the ratio increasing greater than 1, hydroxy groups tend to be present in a number larger than the total number of isocyanate groups and carboxy groups in entire molecular ends of the polyester polyurethane, where the hydroxy groups have lower optical absorptivity as compared with the isocyanate groups and the carboxy groups. In this case, the polyester polyurethane therefore tends to have higher transparency. In the polyester polyurethane in the pressure-sensitive adhesive layer, the ratio of the total number of hydroxy groups of the polyhydric alcohol to the sum of the total number of isocyanate groups of the multifunctional isocyanate and the total number of carboxy groups of the polycarboxylic acid is preferably 0.5 to 1.5, more preferably 0.7 to 1.4, furthermore preferably 0.7 to 1.3, and still more preferably 0.8 to 1.2. These are preferred from the viewpoint of balance between the cohesiveness and transparency in the polyester polyurethane, consequently, from the viewpoint of balance between the cohesiveness and transparency of the pressure-sensitive adhesive layer containing the polyester polyurethane.

In the polyester polyurethane in the pressure-sensitive adhesive layer, a ratio is preferably 0.5 to 1.0, where the ratio is the ratio of the total number of isocyanate groups assigned to multifunctional isocyanate-derived units (namely, the total number of isocyanate groups of a multifunctional isocyanate to constitute the multifunctional isocyanate-derived units) to the total number of carboxy groups assigned to polycarboxylic acid-derived units (namely, the total number of carboxy groups of a polycarboxylic acid to form the polycarboxylic acid-derived units). This configuration is advantageous for allowing the pressure-sensitive adhesive layer in the identification sheet to actually have both high transparency and good cohesiveness.

In the polyester-polyether polyurethane in the pressure-sensitive adhesive layer, a ratio is preferably 1.5 to 9.0, where the ratio is the ratio of the total number of hydroxy groups assigned to first polyhydric alcohol-derived units (namely, the total number of hydroxy groups of a first polyhydric alcohol to constitute the first polyhydric alcohol-derived units) to the total number of hydroxy groups assigned to second polyhydric alcohol-derived units (namely, the total number of hydroxy groups of a second polyhydric alcohol to constitute the second polyhydric alcohol-derived units). This configuration is advantageous for allowing the pressure-sensitive adhesive layer in the identification sheet to surely have high thermal stability, low fluidity, and high transparency and to still have both good cohesiveness and good flexibility.

Preferably, in the polyester-polyether polyurethane in the pressure-sensitive adhesive layer, the second polyhydric alcohol to constitute second polyhydric alcohol-derived units is a multimer that is a polymer derived from a single type of monomer, and a ratio is 0.1 to 0.4, where the ratio is the ratio of the total number of hydroxy groups assigned to first polyhydric alcohol-derived units (namely, the total number of hydroxy groups of the first polyhydric alcohol to constitute the first polyhydric alcohol-derived units) to the total number of units derived from the single type of monomer in the second polyhydric alcohol or in the second polyhydric alcohol-derived units. This configuration is advantageous for balancing between the technical effects by the first polyhydric alcohol-derived units and the technical effects by the second polyhydric alcohol-derived units. In addition, the configuration is advantageous for restraining excessive hydrophilicity of the polyester-polyether polyurethane in the pressure-sensitive adhesive layer, consequently, for restraining excessive hydrophilicity of the pressure-sensitive adhesive layer, and advantageous for allowing the adhesive face in the identification sheet to surely collect a hydrophobic component (such as an oil component in a secretion that forms fingerprints).

Preferably, the multifunctional isocyanate is an aliphatic or alicyclic multifunctional isocyanate. The configuration is advantageous for allowing the pressure-sensitive adhesive layer in the identification sheet to actually have high transparency. More preferably, the multifunctional isocyanate is at least one selected from the group consisting of hexamethylene diisocyanate, 1,3-bis(isocyanatomethyl)cyclohexane, isophorone diisocyanate, 4,4'-methylenebis(cyclohexyl isocyanate), and hydrogenated diphenylmethane diisocyanate. Among them, hexamethylene diisocyanate is particularly preferred as the multifunctional isocyanate, for allowing the polyester polyurethane to actually have not only high transparency, but also appropriate cohesiveness and consequently for allowing the pressure-sensitive adhesive layer in the identification sheet to actually have not only high transparency, but also appropriate cohesiveness. This is probably because hexamethylene diisocyanate gives a polyester polyurethane having appropriate balance between the number of isocyanate groups to constitute hydrophilic urethane bonds and the number of methylene groups to constitute a hydrophobic skeleton, where the balance is appropriate for the polyester polyurethane when used to constitute the pressure-sensitive adhesive layer for use in the identification sheet.

Preferably, the polycarboxylic acid is an aliphatic or alicyclic polycarboxylic acid. This configuration is advantageous for allowing the pressure-sensitive adhesive layer in the identification sheet to actually have high transparency. More preferably, the polycarboxylic acid is adipic acid. Assume that the polyester polyurethane includes units derived from hexamethylene diisocyanate (first units) and units derived from adipic acid (second units). In this case, a pair of urethane bonds and a pair of ester bonds respectively in each first unit and in each second unit tend to form two pairs of hydrogen bonds. This is because the distance between the pair of urethane bonds in the first unit approximates to the distance between the pair of ester bonds in the second unit. The interaction as above is usable as one of approaches to control the cohesiveness of the polyester polyurethane. Thus, the combination use of hexamethylene diisocyanate and adipic acid as monomers to form the polyester polyurethane is preferred from the viewpoint of controlling the cohesiveness of the polyester polyurethane, or of the pressure-sensitive adhesive layer containing the polyester polyurethane.

Preferably, the first polyhydric alcohol is an aliphatic or alicyclic polyhydric alcohol. This configuration is advantageous for allowing the pressure-sensitive adhesive layer in the identification sheet to actually have high transparency. More preferably, the first polyhydric alcohol is neopentyl glycol. Neopentyl glycol, which has a branched chain structure, is expected to have a higher action of relaxing or lowering the cohesiveness between polyester polyurethane molecular chains when the neopentyl glycol is incorporated in the polyester polyurethane, as compared with linear polyols. The cohesiveness lowering action as above is usable as one of approaches to control the cohesiveness of the polyester polyurethane. Accordingly, the use of neopentyl glycol as a polyol component to form the polyester polyurethane is preferred from the viewpoint of controlling the cohesiveness of the polyester polyurethane, or of the pressure-sensitive adhesive layer containing the polyester polyurethane.

Preferably, the second polyhydric alcohol is an aliphatic or alicyclic polyhydric alcohol containing an ether bond. This configuration is advantageous for allowing the pressure-sensitive adhesive layer in the identification sheet to actually have high transparency. More preferably, the second polyhydric alcohol is a polypropylene glycol. The polypropylene glycol not only has high flexibility, but also is readily designable to have multiple functions and/or to have a high molecular weight. Thus, the use of the polypropylene glycol as a polyol component to form the polyester-polyether polyurethane is advantageous for providing a high degree of freedom in molecular designing of the polyester-polyether polyurethane while imparting flexibility to the polyester-polyether polyurethane.

BRIEF DESCRIPTION OF DRAWINGS

FIG. 1 is a plan view of an identification sheet according to one embodiment of the present invention;

FIG. 2 is another plan view of the identification sheet illustrated in FIG. 1;

FIG. 3 is a partial enlarged cross-sectional view of the identification sheet illustrated in FIG. 1;

FIG. 4 illustrates one modification of the identification sheet illustrated in FIG. 1; and FIG. 5 is a partial enlarged cross-sectional view of an identification sheet according to another embodiment of the present invention.

DESCRIPTION OF EMBODIMENTS

FIGS. 1 to 3 illustrate an identification sheet X1 according to one embodiment of the present invention. FIGS. 1, 2, and 3 are a plan view, another plan view, and a partial enlarged cross-sectional view, respectively, of the identification sheet X1.

The identification sheet X1 includes a backing sheet 10 and a pressure-sensitive adhesive sheet 20, which are separable from each other. The identification sheet X1 has an outer face 10a defined by the backing sheet 10, and an outer face 20a defined by the pressure-sensitive adhesive sheet 20.

The outer face 10a defined by the backing sheet 10 bears a distinguishing mark M1, which carries distinguishing information. The outer face 10a bearing the distinguishing mark M1 may be covered with a transparent protective film. The outer face 20a defined by the pressure-sensitive adhesive sheet 20 bears a distinguishing mark M2, which carries distinguishing information. The outer face 20a bearing the distinguishing mark M2 may be covered with a transparent protective film. The distinguishing marks M1 and M2 are independently engraved marks. As used herein, the term "engraved mark" refers to a mark formed by an engraving technique which gives a concave shape in a face to be marked. Non-limiting examples of the engraving technique include laser marking and air pen marking. The laser marking may be performed typically using any of $CO_2$ laser, UV laser, green laser, and fiber laser. The air pen marking is a marking technique that uses dot pressurization with a super-hard stylus vibrating at high speed.

These distinguishing marks M1 and M2 are designed to correspond to each other, so as to function as a pair of cross-check information to determine whether a backing sheet 10 with the distinguishing mark M1 and a pressure-sensitive adhesive sheet 20 with the distinguishing mark M2 correspond to each other. Specifically, in an embodiment, the distinguishing marks M1 and M2 have pattern shapes identical to each other and function as a pair of cross-check information. In another embodiment, the distinguishing marks M1 and M2 have pattern shapes different from each other and function as a pair of cross-check information. In still another embodiment, the identification sheet X1 is designed so as to have a partial region that is transparent all over the thickness direction of the sheet X1. In this embodiment, the distinguishing mark M1 is disposed in the partial region in the outer face 10a; the distinguishing mark M2 is disposed in the partial region in the outer face 20a; and these distinguishing marks M1 and M2 can be seen at one time from the outer face 10a side or from the outer face 20a side and function as a pair of cross-check information. Non-limiting examples of elementary shapes to be included in the pattern shapes of the distinguishing marks M1 and M2 include numerical characters, alphabetic characters, hiragana characters, katakana characters, kanji characters, symbols, bar codes, QR Codes (quick response codes), and other two-dimensional codes. Examples of the bar codes include one-dimensional bar codes and two-dimensional bar codes. The distinguishing marks M1 and M2 may each independently have a pattern shape including elementary shapes of the same kind, or a patter shape including elementary shapes of different kinds. FIGS. 1 to 3 illustrate an embodiment in which the distinguishing marks M1 and M2 are both marks resulting from laser marking, have pattern shapes being identical to each other and including a sequence of numerical characters, and function as a pair of cross-check information.

The backing sheet 10 has a multilayer structure including a base layer 11, a writable layer 12, a background layer 13, and a release layer 14, as illustrated in FIG. 3.

The base layer 11 of the backing sheet 10 is a portion that functions as a support or substrate in the backing sheet 10. Examples of a material or materials to constitute the base layer 11 include, but are not limited to, synthetic paper, woodfree paper, Kent paper, polyester films, and polyolefin films. Non-limiting examples of the polyester films include polyethylene terephthalate films and polybutylene terephthalate films. Non-limiting examples of the polyolefin films include polyethylene films and polypropylene films. The base layer 11 has a thickness of typically 2.5 to 500 μm, preferably 25 to 300 μm, more preferably 50 to 200 μm, and furthermore preferably 100 to 150 μm.

The writable layer 12 of the backing sheet 10 is a portion that provides a writable surface. The outer surface defined by the writable layer 12 defines or constitutes the outer face 10a, which can be an outer surface of the backing sheet 10 or the identification sheet X1. In this embodiment, the outer surface is a writable surface of the identification sheet X1 or the backing sheet 10. The writable surface provided by the writable layer 12 includes at least one preprinted box in which a set of information relating to collection of a target material is, for example, to be recorded, as illustrated in FIG. 1. Each preprinted box typically includes blanks for a date, for a collection number, for a case name, for a collection place, for a collected material name (collected item name), for a collector's signature and seal, and for a witness's signature and seal. The preprinted box as above is formed typically by printing on the writable layer 12. Non-limiting examples of a material or materials to constitute the writable layer 12 include polyurethane inks, polyester inks, acrylic inks, and polystyrene inks, each of which is colored white or whitish. The material(s) to constitute the writable layer 12 is preferably selected from polyurethane inks, from the viewpoint of providing high heat resistance of the writable layer 12. For example, assume that the distinguishing mark M1 is to be formed at the outer face 10a by laser marking. In this case, the higher the heat resistance of the constituent material of the writable layer 12 is, the more preferred so as to restrain collapse typically of drawn lines due to excessive melting of the constituent material of the writable layer 12 upon laser marking. The writable layer 12 as above has a thickness of typically 0.01 to 100 μm, preferably 0.1 to 30 μm, and more preferably 0.5 to 10 μm.

The background layer 13 of the backing sheet 10 is a colored layer and is typically colored black or white. Non-limiting examples of a material or materials to constitute the background layer 13 include polyurethane inks, polyester inks, acrylic inks, and polystyrene inks. The background layer 13 has a thickness of typically 0.01 to 100 μm, preferably 0.1 to 50 μm, and more preferably 0.5 to 30 μm.

The release layer 14 of the backing sheet 10 is a layer that surely offers releasability (removability) between the backing sheet 10 and the pressure-sensitive adhesive sheet 20. The release layer 14 is typically transparent. A non-limiting example of a material or materials to constitute the release layer 14 is a transparent plastic film. Non-limiting examples of the plastic film include polyethylene films and polyethylene terephthalate films. The release layer 14 has a thickness of typically 2.5 to 500 μm, preferably 10 to 250 μm, and more preferably 20 to 125 μm. In the release layer 14, the surface facing the pressure-sensitive adhesive sheet 20 defines a mount face 10b of the backing sheet 10.

The pressure-sensitive adhesive sheet 20 of the identification sheet X1 has a multilayer structure including a substrate layer 21 and a pressure-sensitive adhesive layer 22, as illustrated in FIG. 3.

The substrate layer 21 of the pressure-sensitive adhesive sheet 20 is a portion that serves as a carrier (support) in the pressure-sensitive adhesive sheet 20. The outer surface defined by the substrate layer 21 constitutes the outer face 20a, which can serves as one outer surface of the pressure-sensitive adhesive sheet 20 or the identification sheet X1. The higher the transparency of the substrate layer 21 is, the more preferred. This is preferred from the viewpoint of surely providing the visibility of a target material when held between the backing sheet 10 and the pressure-sensitive adhesive sheet 20 in the identification sheet X1 and seen from the pressure-sensitive adhesive sheet 20 side. Assume that laser marking is employed to form the distinguishing mark M2 at the outer face 20a. In this case, the higher the transparency of the substrate layer 21 is, the less the lines or other marks tend to be colored upon laser marking. The higher the transparency of the substrate layer 21 is, the better, also in the case where elimination or minimization of the coloring is required. Examples of a material or materials to constitute the substrate layer 21 include, but are not limited to, polyester films and polyolefin films. Non-limiting examples of the polyester films include polyethylene terephthalate films and polybutylene terephthalate films.

Non-limiting examples of the polyolefin films include polyethylene films and polypropylene films. The constituent material of the substrate layer 21 is preferably selected from polyethylene terephthalate films, from the viewpoint of allowing the substrate layer 21 to have high transparency. The substrate layer 21 has a thickness of preferably 2.5 to 500 µm, more preferably 25 to 250 µm, and furthermore preferably 50 to 125 µm.

The pressure-sensitive adhesive layer 22 of the pressure-sensitive adhesive sheet 20 has an adhesive face 22a and is removable from (attachable to and detachable from) the mount face 10b of the backing sheet 10. The pressure-sensitive adhesive layer 22 may be made from a pressure-sensitive adhesive composition containing a pressure-sensitive adhesive as a principal component. As used herein, the term "principal component" refers to a component that is present in a largest weight proportion among components contained therein. Non-limiting examples of the pressure-sensitive adhesive contained in the pressure-sensitive adhesive layer 22 include polyurethanes as urethane pressure-sensitive adhesives; acrylic polymers as acrylic pressure-sensitive adhesives; rubber pressure-sensitive adhesives; silicone pressure-sensitive adhesives; and gelatin pressure-sensitive adhesives. The higher the transparency of the pressure-sensitive adhesive layer 22 is, the more preferred. This is preferred from the viewpoint of surely providing the visibility of a target material when held between the backing sheet 10 and the pressure-sensitive adhesive sheet 20 in the identification sheet X1 and seen from the pressure-sensitive adhesive sheet 20 side. The pressure-sensitive adhesive layer 22 has a storage modulus of typically $3 \times 10^3$ to $9 \times 10^6$ Pa, preferably $3 \times 10^3$ to $9 \times 10^5$ Pa, and more preferably $3 \times 10^3$ to $9 \times 10^4$ Pa. The pressure-sensitive adhesive layer 22 has an adhesive strength of typically 0.01 to 10 N/20 mm, preferably 0.03 to 5 N/20 mm, more preferably 0.05 to 2 N/20 mm, and furthermore preferably 0.07 to 0.7 N/20 mm. The pressure-sensitive adhesive layer 22 has a thickness of typically 10 to 1000 µm, more preferably 150 to 800 µm, and furthermore preferably 200 to 500 µm.

The pressure-sensitive adhesive contained in the pressure-sensitive adhesive layer 22 is preferably a polyurethane, which serves as a urethane pressure-sensitive adhesive. The polyurethane is a polymer containing many urethane bonds in its molecular chain, and is a polymer resulting from polymerization of a polyhydric alcohol in combination with a multifunctional isocyanate, and, optionally as needed, a compound containing an active hydrogen group. Non-limiting examples of the polyhydric alcohol include polymer glycols and low-molecular glycols. Non-limiting examples of the multifunctional isocyanate include diisocyanates. Such a polyurethane can be synthetically prepared typically by solution polymerization, emulsion polymerization, or bulk polymerization, according to a so-called prepolymer process, which is a two-step synthesis, or according to a so-called one-shot process, which is a one-step synthesis. The urethane bonds in the polyurethane are each a hydrogen-bonding functional group that contains both a hydrogen donor group and a hydrogen acceptor group. The polyurethane, which contains that kind of hydrogen-bonding functional groups, can form hydrogen bonds between molecular chains to cohere with each other and has relatively high cohesive energy. The polyurethane therefore tends to actually have a high softening temperature and/or a high glass transition temperature, namely, high thermal stability. The configuration, where the pressure-sensitive adhesive layer 22 contains such a polyurethane as a principal component, allows the pressure-sensitive adhesive layer 22 in the identification sheet X1 to readily actually have high thermal stability and/or low fluidity. The high thermal stability and/or the low fluidity of the pressure-sensitive adhesive layer 22 contributes to long-term, stable storage of the target material to be held in the identification sheet X1. Assume that heat transfer to the pressure-sensitive adhesive layer 22 and/or heat evolution in the pressure-sensitive adhesive layer 22 occurs during marking of a distinguishing mark in a process of identification sheet production. In this case, the high thermal stability or high heat resistance of the pressure-sensitive adhesive layer 22 also contributes to eliminating or minimizing deformation and failure, due to the heat, of the pressure-sensitive adhesive layer 22. The polyurethane contained in the pressure-sensitive adhesive layer 22 and serving as a pressure-sensitive adhesive has a softening temperature of preferably 190° C. to 280° C., more preferably 200° C. to 270° C., and furthermore preferably 210° C. to 260° C. The softening temperature of the pressure-sensitive adhesive may be measured typically using a thermomechanical analyzer TMA/SS7100 (trade name, supplied by SII NanoTechnology Inc.). In this measurement, for example, a test piece (6 mm by 6 mm) is prepared by cutting out from a sample pressure-sensitive adhesive sheet having a multilayer structure including a polyethylene terephthalate substrate and a pressure-sensitive adhesive layer (thickness: 290 µm). The measurement is performed in a penetration mode using a needle penetrator probe having a tip diameter of 1 mm under a load of 1470 mN, in which the tip of the probe is brought in contact with the central part of the pressure-sensitive adhesive surface of the test piece. In the measurement, the temperature is raised from a start temperature of 150° C. up to an end temperature of 320° C. at a rate of temperature rise of 10° C./min, in a nitrogen stream at a flow rate of 200 ml/min. The glass transition temperature of the pressure-sensitive adhesive may be measured by differential scanning calorimetry (DSC) in conformity to JIS K 7121: Testing Methods for Transition Temperatures of Plastics.

The polyurethane, when contained as a pressure-sensitive adhesive in the pressure-sensitive adhesive layer 22, is preferably a polyester polyurethane. The polyester polyurethane has ester bonds, which are hydrogen acceptor groups, in addition to urethane bonds as described above. In the polyester polyurethane, the ester bonds less cause molecular chains to cohere with each other, as compared with the urethane bonds. The regulation of the content or proportion of ester bonds in the polyester polyurethane can be used as one of approaches to control the cohesiveness of the polyester polyurethane. Accordingly, the polyester polyurethane, which contains the ester bonds in addition to the urethane bonds, is easily controllable on the cohesive force between its molecular chains within such a range as to offer high thermal stability. In addition, the polyester polyurethane can be formed from material monomers selectable from among a wide variety of practically easily available high-purity monomers. With increasing purities of material monomers, a polymer resulting from the material monomers tends to have higher transparency. Accordingly, such a polyester polyurethane, which can be formed from material monomers selectable from among a wide variety of practically easily available high-purity monomers, tends to actually have high transparency. The configuration, where the polyester polyurethane is contained as a principal component in the pressure-sensitive adhesive layer 22, tends to allow the pressure-sensitive adhesive layer 22 to surely have high thermal stability and/or low fluidity, to still be readily controllable on cohesiveness, and to readily actually have high transparency. Control of the cohesiveness of the pressure-sensitive adhesive layer 22 contributes to allowing the pressure-sensitive adhesive layer 22 to actually have good adhesive strength and to less leave adhesive residue on an adherend after the pressure-sensitive adhesive sheet 20 or the pressure-sensitive adhesive layer 22 is removed from the adherend. Assume that laser marking is employed to form at least one of the distinguishing mark M1 and the distinguishing mark M2 in the process of identification sheet X1 production. In this case, the high transparency of the pressure-sensitive adhesive layer 22 contributes to restraining heat evolution in the pressure-sensitive adhesive layer 22 due to laser beam absorption, and contributes to eliminating or minimizing thermal deformation and thermal failure of the pressure-sensitive adhesive layer 22.

The polyester polyurethane, when contained as a pressure-sensitive adhesive in the pressure-sensitive adhesive layer 22, preferably includes units derived from a multifunctional isocyanate, units derived from a polycarboxylic acid, and units derived from a first polyhydric alcohol. This configuration can appropriately give the polyester polyurethane with the technical effects.

The polyester polyurethane, when contained as a pressure-sensitive adhesive in the pressure-sensitive adhesive layer 22, is preferably a polyester-polyether polyurethane. The polyester-polyether polyurethane contains a polyether skeleton, in addition to urethane bonds and ester bonds as described above. Ether bonds contained in the polyether skeleton have low optical absorptivity and have higher flexibility or mobility as compared with carbon-carbon-carbon bonds. The polyester-polyether polyurethane, which contains such a polyether skeleton in addition to urethane bonds and ester bonds, tends to actually have high transparency and good flexibility while controlling the cohesive force between its molecular chains within such a range as to give high thermal stability. Polyester polyurethanes, to which the polyester-polyether polyurethane belongs, can be formed from material monomers which are selectable from among a wide variety of practically easily available high-purity monomers. Accordingly, the polyester-polyether polyurethane, which belongs to polyester polyurethanes capable of being made from material monomers selectable from among a wide variety of easily available high-purity material monomers, tends to actually have high transparency. The configuration, where the polyester-polyether polyurethane is contained as a principal component in the pressure-sensitive adhesive layer 22, tends to allow the pressure-sensitive adhesive layer 22 in the identification sheet X1 to surely have high thermal stability and/or low fluidity, to have easily controllable cohesiveness, and to still have both high transparency and good flexibility. With increasing flexibility of the pressure-sensitive adhesive layer 22, the adhesive face 22a of the pressure-sensitive adhesive layer 22 more conforms to, and more deforms with, a target material, when the pressure-sensitive adhesive layer 22 or the adhesive face 22a is pressed onto the target material, and the asperities of the target material are more readily transferred onto the pressure-sensitive adhesive layer 22. Balancing between flexibility and thermal stability-low fluidity of the pressure-sensitive adhesive layer 22 in the identification sheet X1 can allow the pressure-sensitive adhesive layer 22 or the adhesive face 22a to actually have such tackiness as to adhere to the target material with good conformity to the asperities and can still restrain so-called stringiness of the pressure-sensitive adhesive between an adherend and the adhesive face 22a upon removal of the pressure-sensitive adhesive layer 22 from the adherend.

The polyester-polyether polyurethane, when contained as a pressure-sensitive adhesive in the pressure-sensitive adhesive layer 22, preferably includes units derived from a multifunctional isocyanate, units derived from a polycarboxylic acid, units derived from a first polyhydric alcohol, and units derived from a second polyhydric alcohol containing an ether bond. This configuration can appropriately give the polyester-polyether polyurethane with the technical effects.

Non-limiting examples of the multifunctional isocyanate include hexamethylene diisocyanate (HDI), 1,3-bis(isocyanatomethyl)cyclohexane, isophorone diisocyanate, 4,4'-methylenebis(cyclohexyl isocyanate), diphenylmethane diisocyanate (MDI), tolylene diisocyanate (TDI), xylylene diisocyanate (XDI), hydrogenated MDI, and TDI adducts. The multifunctional isocyanate is preferably selected from aliphatic or alicyclic multifunctional isocyanates. This configuration is advantageous for allowing the pressure-sensitive adhesive layer 22 in the identification sheet X1 to actually have high transparency. More preferably, the multifunctional isocyanate is at least one selected from the group consisting of hexamethylene diisocyanate, 1,3-bis(isocyanatomethyl)cyclohexane, isophorone diisocyanate, 4,4'-methylenebis(cyclohexyl isocyanate), and hydrogenated MDI. Among them, hexamethylene diisocyanate is particularly preferred as the multifunctional isocyanate. This is preferred for allowing the polyester polyurethane to actually have not only high transparency, but also appropriate cohesiveness, and consequently for allowing the pressure-sensitive adhesive layer 22 in the identification sheet X1 to actually have not only high transparency, but also appropriate cohesiveness. This is probably because hexamethylene diisocyanate gives a polyester polyurethane having appropriate balance between the number of isocyanate groups to constitute hydrophilic urethane bonds and the number of methylene groups to constitute a hydrophobic skeleton, where the balance is appropriate for the polyester polyurethane when used to constitute the pressure-sensitive adhesive layer 22 for use in the identification sheet.

Non-limiting examples of the polycarboxylic acid include aliphatic or alicyclic polycarboxylic acids and aromatic polycarboxylic acids. Non-limiting examples of the aliphatic or alicyclic polycarboxylic acids include malonic acid, succinic acid, glutaric acid, adipic acid, and sebacic acid. Non-limiting examples of the aromatic polycarboxylic acids include terephthalic acid and trimellitic acid. The polycarboxylic acid is preferably selected from aliphatic or alicyclic polycarboxylic acids. This configuration is advantageous for allowing the pressure-sensitive adhesive layer 22 in the identification sheet X1 to actually have high transparency. More preferably, the polycarboxylic acid is adipic acid. Assume that the polyester polyurethane includes units derived from hexamethylene diisocyanate (first units) and units derived from adipic acid (second units). In this case, a pair of urethane bonds and a pair of ester bonds respectively in each first unit and in each second unit tend to form two pairs of hydrogen bonds. This is because the distance between the pair of urethane bonds in the first unit approximates to the distance between the pair of ester bonds in the second unit. The interaction as above is usable as one of approaches to control the cohesiveness of the polyester polyurethane. Thus, the combination use of hexamethylene diisocyanate and adipic acid as monomers to form the polyester polyurethane is preferred from the viewpoint of controlling the cohesiveness of the polyester polyurethane or of the pressure-sensitive adhesive layer 22 containing the polyester polyurethane.

Examples of the first polyhydric alcohol include, but are not limited to, aliphatic or alicyclic polyhydric alcohols and aromatic polyhydric alcohols. Non-limiting examples of the aliphatic or alicyclic polyhydric alcohols include ethylene glycol, propylene glycol, butylene glycol, neopentyl glycol, and cyclohexanediol. Non-limiting examples of the aromatic polyhydric alcohols include bisphenol-A and resorcinol. The first polyhydric alcohol is preferably selected from aliphatic or alicyclic polyhydric alcohols. This configuration is advantageous for allowing the pressure-sensitive adhesive layer 22 in the identification sheet X1 to actually have high transparency. More preferably, the first polyhydric alcohol is neopentyl glycol. Neopentyl glycol, which has a branched chain structure, is expected to have a higher action of relaxing or lowering the cohesiveness between polyester polyurethane molecular chains when the neopentyl glycol is incorporated in the polyester polyurethane, as compared with linear polyols. The cohesiveness lowering action as above is usable as one of approaches to control the cohesiveness of the polyester polyurethane. Accordingly, the use of neopentyl glycol as a polyol component to form the polyester polyurethane is preferred from the viewpoint of controlling the cohesiveness of the polyester polyurethane or of the pressure-sensitive adhesive layer 22 containing the polyester polyurethane.

The second polyhydric alcohol is preferably selected from aliphatic or alicyclic polyhydric alcohols containing an ether bond. The aliphatic or alicyclic polyhydric alcohols containing an ether bond may be ones that are crosslinked typically with glycerol or ethylene glycol. Non-limiting examples of the second polyhydric alcohol include polyethylene glycols and polypropylene glycols. The second polyhydric alcohol as above has a number average molecular weight of preferably 300 to 50000, more preferably 500 to 10000, furthermore preferably 500 to 5000, still more preferably 500 to 4000, and still furthermore preferably 1000 to 3000. The "number average molecular weight" herein is a value obtained by gel permeation chromatographic (GPC) measurement and calibration with a polyethylene oxide (PEO) as a standard polymer sample. The configuration as above relating to the second polyhydric alcohol is advantageous for allowing the pressure-sensitive adhesive layer 22 in the identification sheet X1 to actually have high transparency. More preferably, the second polyhydric alcohol is a polypropylene glycol. The polypropylene glycol not only has high flexibility, but also is readily designable to have multiple functions and/or to have a high molecular weight. Thus, the use of the polypropylene glycol as a polyol component to form the polyester-polyether polyurethane is advantageous for providing high degree of freedom in molecular design of the polyester-polyether polyurethane, while imparting flexibility to the polyester-polyether polyurethane.

In the polyester polyurethane (including the polyester-polyether polyurethane), when contained in the pressure-sensitive adhesive layer 22, a first ratio is preferably 0.5 to 1.5, more preferably 0.7 to 1.4, furthermore preferably 0.7 to 1.3, and still more preferably 0.8 to 1.2, where the first ratio is the ratio of the total number of hydroxy groups in the polyhydric alcohol(s) (namely, the total number of hydroxy groups in the polyhydric alcohol(s) to constitute polyhydric alcohol-derived units) to the sum of the total number of isocyanate groups in the multifunctional isocyanate (namely, the total number of isocyanate groups in the multifunctional isocyanate to constitute multifunctional isocyanate-derived units) and the total number of carboxy groups in the polycarboxylic acid (namely, the total number of carboxy groups in the polycarboxylic acid to constitute polycarboxylic acid-derived units). With the ratio (first ratio) approaching 1, the polyester polyurethane tends to have a higher molecular weight and, due to such a high molecular weight, tends to offer higher cohesiveness between molecules of the polyester polyurethane. With the ratio decreasing less than 1, isocyanate groups and carboxy groups tend to be present in a total number larger than the number of hydroxy groups in entire molecular ends of the polyester polyurethane, and, accordingly, the cohesiveness between molecules of the polyester polyurethane tends to be higher, where the cohesiveness is due to the presence of isocyanate groups and carboxy groups, both of which are highly polar groups which relatively highly polarize. With the ratio increasing greater than 1, hydroxy groups tend to be present in a number larger than the total number of isocyanate groups and carboxy groups in entire molecular ends of the polyester polyurethane, where the hydroxy groups have lower optical absorptivity as compared with the isocyanate groups and the carboxy groups. In this case, the polyester polyurethane therefore tends to have higher transparency. In other words, in the polyester polyurethane in the pressure-sensitive adhesive layer 22, the first ratio is preferably 0.5 to 1.5, more preferably 0.7 to 1.4, furthermore preferably 0.7 to 1.3, and still more preferably 0.8 to 1.2, from the viewpoints of balancing between cohesiveness and transparency of the polyester polyurethane, and, consequently, from the viewpoint of balancing between cohesiveness and transparency of the pressure-sensitive adhesive layer 22 containing the polyester polyurethane. The first ratio is the ratio of the total number of hydroxy groups in the polyhydric alcohol(s) to the sum of the total number of isocyanate groups in the multifunctional isocyanate and the total number of carboxy groups in the polycarboxylic acid.

In the polyester polyurethane (including the polyester-polyether polyurethane) in the pressure-sensitive adhesive layer 22, a second ratio is preferably 0.5 to 1.0, where the second ratio is the ratio of the total number of isocyanate groups in the multifunctional isocyanate (namely, the total number of isocyanate groups in the multifunctional isocyanate to constitute multifunctional isocyanate-derived units) to the total number of carboxy groups in the polycarboxylic acid (namely, the total number of carboxy groups in the polycarboxylic acid to constitute polycarboxylic acid-derived units). This configuration is advantageous for allowing the pressure-sensitive adhesive layer 22 in the identification sheet X1 to actually have both high transparency and good cohesiveness.

In the polyester-polyether polyurethane, when contained in the pressure-sensitive adhesive layer 22, a third ratio is preferably 1.5 to 9.0, where the third ratio is the ratio of the total number of hydroxy groups in the first polyhydric alcohol (namely, the total number of hydroxy groups in the first polyhydric alcohol to constitute first-polyhydric alcohol-derived units) to the total number of hydroxy groups in the second polyhydric alcohol (namely, the total number of hydroxy groups in the second polyhydric alcohol to constitute second-polyhydric alcohol-derived units). This configuration is advantageous for allowing the pressure-sensitive adhesive layer 22 in the identification sheet X1 to surely have high thermal stability, low fluidity, and high transparency and to still actually have both good cohesiveness and good flexibility.

Assume that the second polyhydric alcohol to constitute the polyester-polyether polyurethane in the pressure-sensitive adhesive layer 22 is a polypropylene glycol, a polyethylene glycol, or another multimer (polymer) derived from a single type of monomer. In this case, in the polyester-polyether polyurethane, a fourth ratio is preferably 0.1 to 0.4, and more preferably 0.12 to 0.34, where the fourth ratio is the ratio of the total number of hydroxy groups in the first polyhydric alcohol (namely, the total number of hydroxy groups in the first polyhydric alcohol to constitute first-polyhydric alcohol-derived units) to the total number of units derived from the single type of monomer in the second polyhydric alcohol, which is the multimer. The fourth ratio, which relates to the first and second polyhydric alcohols to form the polyester-polyether polyurethane, is preferably 0.1 to 0.4, and more preferably 0.12 to 0.34, for balancing between the technical effects mentioned relating to the first polyhydric alcohol and the technical effects mentioned relating to the second polyhydric alcohol. In addition, the fourth ratio is preferably 0.1 or more. This is preferred for restraining excessive hydrophilicity of the polyester-polyether polyurethane in the pressure-sensitive adhesive layer 22 and, consequently, for restraining excessive hydrophilicity of the pressure-sensitive adhesive layer 22, and advantageous for allowing the adhesive face 22a in the identification sheet X1 to surely have collectability of a hydrophobic component (such as an oil component in a secretion that forms fingerprints).

The first ratio, the second ratio, the third ratio, and the fourth ratio are values each of which may be determined on the basis of the abundance ratios or relative numbers of the various substructures or functional groups in the polymer. The abundance ratio or relative number of each of various substructures or functional groups in a polymer can be controlled by adjusting relative amounts or proportions of various material monomers used for the synthesis of the polymer. The abundance ratio or relative number of each of various substructures or functional groups in the resulting polymer may be determined typically through a process as follows.

Initially, the polymer to be analyzed (analyte polymer) is purified. For example, a material containing the analyte polymer and constituting the pressure-sensitive adhesive layer is stirred in a predetermined solvent to give a crude polymer solution. After removing solvent-insoluble matter from the solution by filtration, a solvent-soluble, low molecular weight non-polymer component is removed from the solution by gel permeation chromatography (GPC) to give a polymer-containing solution, from which the solvent is distilled off. The solvent is selected or determined depending on properties of the polymer, such as solubility. The solvent may be selected typically from dimethylformamide, chloroform, methylene chloride, tetrahydrofuran, acetone, dimethyl sulfoxide, methanol, ethanol, toluene, and water. Next, a sample solution is prepared by dissolving the analyte polymer after the purification in a predetermined deuterated solvent for NMR measurement. Alternatively, a sample solution may be prepared by subjecting the analyte polymer to a hydrolysis treatment for the hydrolysis of ester bonds and urethane bonds in the analyte polymer to give various fragments or monomers derived from the analyte polymer, and dissolving the fragments or monomers in a deuterated solvent. Further alternatively, a sample solution may be prepared by subjecting the analyte polymer to a solvolysis treatment using a deuterated solvent that can solvolyze ester bonds and urethane bonds in the analyte polymer to give a deuterated solvent containing various fragments or monomers derived from the analyte polymer, and preparing the sample solution from the resulting deuterated solvent. The various fragments or monomers resulting from the hydrolysis treatment or solvolysis treatment and being derived from the analyte polymer may be fractionated into fractions by GPC, and sample solutions for NMR measurement may be individually prepared on the fraction-to-fraction basis. The deuterated solvent is selected or determined depending on the properties of the polymer, such as solubility. The deuterated solvent for use herein may be selected typically from deuterated chloroform, deuterated methylene chloride, deuterated tetrahydrofuran, deuterated acetone, deuterated dimethyl sulfoxide, deuterated N,N-dimethylformamide, deuterated methanol, deuterated ethanol, and heavy water. Next, the sample solution is subjected to $^1$H-NMR measurement to give a $^1$H-NMR spectrum. The resulting spectrum is subjected to waveform separation, and intensity ratios (signal integral ratios) of signals assigned to various substructures or functional groups are determined. Then, on the basis of the signal intensity ratios, the abundance ratios or relative numbers of the various substructures or functional groups in the polymer are determined. The abundance ratios or relative numbers of various substructures or functional groups in the analyte polymer can be determined typically by the above procedure.

Assume that the pressure-sensitive adhesive layer 22 contains an acrylic polymer, which serves as an acrylic pressure-sensitive adhesive. In this case, the acrylic polymer may typically include units derived from a first alkyl (meth) acrylate containing a $C_1$-$C_4$ alkyl group, and units derived from a second alkyl (meth)acrylate containing a $C_6$-$C_{14}$ alkyl group. As used herein, the term "(meth)acryl(ate)" refers to "acryl(ate)" and/or "methacryl(ate)". Non-limiting examples of the first alkyl (meth)acrylate include methyl (meth)acrylate, ethyl (meth)acrylate, propyl (meth)acrylate, isopropyl (meth)acrylate, n-butyl (meth)acrylate, isobutyl (meth)acrylate, s-butyl (meth)acrylate, and t-butyl (meth) acrylate. Each of different first alkyl (meth)acrylates may be used alone or in combination to form the acrylic polymer. Non-limiting examples of the second alkyl (meth)acrylate include hexyl (meth)acrylate, isohexyl (meth)acrylate, heptyl (meth)acrylate, isoheptyl (meth)acrylate, octyl (meth) acrylate, 2-ethylhexyl (meth)acrylate, isooctyl (meth)acrylate, nonyl (meth)acrylate, isononyl (meth)acrylate, decyl (meth)acrylate, isodecyl (meth)acrylate, undecyl (meth) acrylate, isoundecyl (meth)acrylate, dodecyl (meth)acrylate, isododecyl (meth)acrylate, tridecyl (meth)acrylate, isotridecyl (meth)acrylate, tetradecyl (meth)acrylate, and isotetradecyl (meth)acrylate. Each of different second alkyl (meth) acrylates may be used alone or in combination to form the acrylic polymer. The acrylic polymer preferably includes units derived from a polar-group-containing monomer. Examples of the polar-group-containing monomer include, but are not limited to, carboxy-containing monomers, hydroxy-containing monomers, amido-containing monomers, amino-containing monomers, and cyano-containing monomers. Non-limiting examples of the carboxy-containing monomers include (meth)acrylic acid, itaconic acid, maleic acid, fumaric acid, and crotonic acid. Non-limiting examples of the hydroxy-containing monomers include 2-hydroxyethyl (meth)acrylate, 3-hydroxypropyl (meth) acrylate, 4-hydroxybutyl (meth)acrylate, and 6-hydroxyhexyl (meth)acrylate. Non-limiting examples of the amido-containing monomers include (meth)acrylamide, N,N-dimethyl(meth)acrylamide, N-methylol(meth)acrylamide, N-methoxymethyl(meth)acrylamide, N-butoxymethyl (meth)acrylamide, and N-hydroxyethyl(meth)acrylamide. Non-limiting examples of the amino-containing monomers include aminoethyl (meth)acrylate, dimethylaminoethyl (meth)acrylate, and t-butylaminoethyl (meth)acrylates. Non-limiting examples of the cyano-containing monomers include acrylonitrile and methacrylonitrile. Each of different polar-group-containing monomers may be used alone or in combination to form the acrylic polymer.

Assume that the pressure-sensitive adhesive layer 22 contains a rubber pressure-sensitive adhesive. In this case, Examples of the rubber pressure-sensitive adhesive include, but are not limited to, synthetic rubbers such as diene synthetic rubbers and non-diene synthetic rubbers; and natural rubbers. Non-limiting examples of the diene synthetic rubbers include isoprene rubber, butadiene rubber, styrene-butadiene rubber, and chloroprene rubber. Non-limiting examples of the non-diene rubbers include isobutylene-isoprene rubber, ethylene-propylene rubber, urethane rubber, and silicone rubber.

The pressure-sensitive adhesive layer 22 may further include an antioxidant and/or a so-called photostabilizer, in addition to the pressure-sensitive adhesive.

The identification sheet X1 having the configurations as above may be produced typically by the following procedure. Initially, the backing sheet 10 and the pressure-sensitive adhesive sheet 20 are individually prepared. The backing sheet 10 can be prepared by forming and laminating the writable layer 12 onto the base layer 11, and forming and laminating the background layer 13 and the release layer 14 onto the base layer 11. The writable layer 12 and the background layer 13 may be formed typically by a printing technique. The release layer 14 may be formed typically by a technique such as dry lamination or extrusion lamination. The pressure-sensitive adhesive sheet 20 may be formed typically by applying a pressure-sensitive adhesive composition onto the substrate layer 21 and drying the applied pressure-sensitive adhesive composition. In the production of the identification sheet X1, next, the mount face 10b in the backing sheet 10 is laminated onto the adhesive face 22a in the pressure-sensitive adhesive sheet 20. Next, the distinguishing mark M1 is formed at the outer face 10a defined by the backing sheet 10, and the distinguishing mark M2 is formed at the outer face 20a defined by the pressure-sensitive adhesive sheet 20. Non-limiting examples of the marking technique include laser marking and air pen marking. The laser marking may be performed typically using any of $CO_2$ laser, UV laser, green laser, and fiber laser. The air pen marking is a marking technique that uses dot pressurization with a superhard stylus vibrating at high speed. After the distinguishing mark M1 is formed, a transparent protective film may be formed so as to cover the outer face 10a of the backing sheet 10. Likewise, after the distinguishing mark M2 is formed, a transparent protective film may be formed so as to cover the outer face 20a of the pressure-sensitive adhesive sheet 20. The identification sheet X1 may be produced typically by the above procedure.

Using the identification sheet X1, a target material may be collected typically by the following procedure. The pressure-sensitive adhesive sheet 20 with the distinguishing mark M2 at the outer face 20a is removed from the mount face 10b of the backing sheet 10 with the distinguishing mark M1 at the outer face 10a. The target material is then attached to the exposed pressure-sensitive adhesive layer 22 or the adhesive face 22a of the pressure-sensitive adhesive sheet 20. Non-limiting examples of the target material include fingerprints, footprints, tire marks, and hairs. Assume that, among fingerprints left typically at a crime scene, a latent fingerprint is to be collected as the target material, where the latent fingerprint is invisible to the naked eye. In this case, for example, a predetermined surface or region where the presence of the latent fingerprint is estimated is subjected to a treatment using a fine powder such as a fine aluminum powder. When the latent fingerprint is present in the region, the treatment allows the fine powder to be attached to the latent fingerprint to thereby visualize the pattern shape (including ridges) of the fingerprint. The adhesive face 22a of the pressure-sensitive adhesive sheet 20, which has been removed from the backing sheet 10, is pressed to, and then removed from, the region. Thus, the visualized fingerprint is transferred onto the adhesive face 22a of the pressure-sensitive adhesive sheet 20. The collection of such a fingerprint may be performed by a technique using an Egyptian blue pigment (EB), in which the latent fingerprint is collected at the adhesive face 22a of the pressure-sensitive adhesive sheet 20, and is then acted upon by a predetermined treatment liquid to color and visualize (develop) the pattern shape of the fingerprint. The resulting pressure-sensitive adhesive sheet 20 with the distinguishing mark M2, to which the target material such as a fingerprint is attached typically by the above procedure, is then laminated again onto the mount face 10b of the original backing sheet 10 with the distinguishing mark M1. In the lamination, the adhesive face 22a bearing the target material is attached onto the mount face 10b. In the preprinted box at the outer face 10a of the backing sheet 10, data or information relating to the collection of the target material is written or recorded, and a collector and a witness individually sign and seal therein, where the data include date, collection number, case name, collection place, and collected material name (item name).

In the identification sheet X1, the distinguishing mark M1 at the backing sheet 10 and the distinguishing mark M2 at the pressure-sensitive adhesive sheet 20, where the two marks correspond to each other, form a pair in the single identification sheet. This certifies that the backing sheet 10 and the pressure-sensitive adhesive sheet 20 correspond to each other. Assume that, in the identification sheet X1 after the collection of the target material, the pressure-sensitive adhesive sheet 20, which bears the true target material and adheres to the backing sheet 10, is removed and replaced with another pressure-sensitive adhesive sheet, where the other pressure-sensitive adhesive sheet is a pressure-sensitive adhesive sheet that lacks the distinguishing mark M2 corresponding to the distinguishing mark M1 of the backing sheet 10. In this case, there can be determined the absence of mutual correspondence between the other pressure-sensitive adhesive sheet after replacement and the backing sheet 10. This is because the other pressure-sensitive adhesive sheet lacks the distinguishing mark M2 corresponding to the distinguishing mark M1 of the backing sheet 10. Assume that, in the identification sheet X1 after the collection of the target material, the backing sheet, to which the pressure-sensitive adhesive sheet 20 bearing the true target material adheres and on which data such as various information for the target material are recorded, is removed and replaced with another backing sheet, where the other backing sheet is a backing sheet that lacks the distinguishing mark M1 corresponding to the distinguishing mark M2 of the pressure-sensitive adhesive sheet 20. In this case, there can be determined the absence of mutual correspondence between the other backing sheet after replacement and the pressure-sensitive adhesive sheet 20. This is because the other backing sheet lacks the distinguishing mark M1 corresponding to the distinguishing mark M2 of the pressure-sensitive adhesive sheet 20. Namely, if the identification sheet X1 undergoes such a replacement as above, the replacement can be detected or recognized. This is because the identification sheet X1 includes the backing sheet 10 and the pressure-sensitive adhesive sheet 20, where the backing sheet 10 bears the distinguishing mark M1, which is one of a pair of cross-check information; and the pressure-sensitive adhesive sheet 20 bears the distinguishing mark M2, which is the other of the pair of cross-check information. The identification sheet X1 as above is suitable for restraining a tampering act on the identification sheet after the collection of the target material and for restraining the mistaking of the pressure-sensitive adhesive sheet 20 or the backing sheet 10 for another one during a collecting process and an identifying operation for the target material. Consequently, the identification sheet X1 is suitable for surely providing the admissibility of evidence required of the target material collected typically in a criminal case.

In addition, in the identification sheet X1, the distinguishing mark M1 has been formed at the outer face 10a of the backing sheet 10, separately from the distinguishing mark M2; and the distinguishing mark M2 has been formed at the outer face 20a of the pressure-sensitive adhesive sheet 20, separately from the distinguishing mark M1. The distinguishing mark M1 in the identification sheet X1 is neither one formed by copying as a result of a transferring action of a coloring component constituting part of another distinguishing mark; nor one formed by copying as a result of a physical and/or chemical reaction caused typically by local heating, pressurization, or photoirradiation in the formation of another distinguishing mark. The distinguishing mark M2 in the identification sheet X1 is neither one formed by copying as a result of a transferring action of a coloring component constituting part of another distinguishing mark; nor one formed by copying as a result of a physical and/or chemical reaction caused typically by local heating, pressurization, or photoirradiation in the formation of another distinguishing mark. The distinguishing marks M1 and M2 are engraved marks individually or separately formed or engraved in the identification sheet X1. This configuration is advantageous for restraining or avoiding the deterioration of the distinguishing marks M1 and M2. Accordingly, the configuration is advantageous for allowing the distinguishing marks M1 and M2 to keep on functioning as a pair of cross-check information so as to determine the mutual correspondence between a backing sheet 10 with the distinguishing mark M1 and a pressure-sensitive adhesive sheet 20 with the distinguishing mark M2.

As described above, the identification sheet X1 is suitable for restraining a tampering act on the identification sheet after the collection of the target material and for restraining the mistaking of the pressure-sensitive adhesive sheet 20 or the backing sheet 10 for another one during a collecting process and an identifying operation for the target material. Consequently, the identification sheet X1 is suitable for keeping on surely providing the admissibility of evidence of the collected target material, where the admissibility of evidence is required typically in a criminal case.

The configuration, where the distinguishing marks M1 and M2 in the identification sheet X1 are engraved marks, is advantageous for allowing faces to be marked (outer faces 10a and 20a) to less undergo a shape change (such as formation of scratch marks) other than the formed distinguishing marks M1 and M2. For example, scratch marks, if present in the outer face 20a defined by the transparent pressure-sensitive adhesive sheet 20, may impede the operation to identify the target material (such as fingerprints) collected by the identification sheet X1.

In addition, when laser marking is employed to form at least one of the distinguishing mark M1 and the distinguishing mark M2, the pattern shape of the distinguishing mark to be formed can be designed or determined with high degree of freedom. This contributes to higher productivity of the identification sheet.

The configuration, where the identification sheet X1 bears or includes an engraved mark formed by laser marking as at least one of the distinguishing mark M1 and the distinguishing mark M2, is also advantageous for surely providing removability or releasability between the backing sheet 10 and the pressure-sensitive adhesive sheet 20. Assume that, in an identification sheet including a backing sheet and a pressure-sensitive adhesive sheet laminated on each other, a laser mark is formed as a through hole penetrating the backing sheet by laser irradiation from the backing sheet side, or a laser mark is formed as a through hole penetrating the pressure-sensitive adhesive sheet by laser irradiation from the pressure-sensitive adhesive sheet side, or a laser mark is formed as a through hole penetrating the entire identification sheet by laser irradiation. In these cases, the pressure-sensitive adhesive is softened and melted at or around an area, in which the through hole is formed, in a surface of the pressure-sensitive adhesive layer of the pressure-sensitive adhesive sheet, where the surface faces the backing sheet. Thus, the pressure-sensitive adhesive layer is liable to fuse to the backing sheet in the area. The fusion, if occurring, may impede the separation, namely, the removal between the backing sheet and the pressure-sensitive adhesive sheet, and/or may cause the pressure-sensitive adhesive layer to be significantly damaged, because the pressure-sensitive adhesive layer at the fused portion is pulled by the backing sheet upon removal. The configuration, where the identification sheet X1 bears or includes an engraved mark formed by laser marking as at least one of the distinguishing mark M1 and the distinguishing mark M2, is advantageous for avoiding or minimizing the occurrence of local fusion between the backing sheet 10 and the pressure-sensitive adhesive sheet 20 and for surely providing removability between the two sheets. Softening and melting of the pressure-sensitive adhesive in the adhesive face causes deformation of the softened-melted area in the pressure-sensitive adhesive layer. The resulting deformation or unevenness in the adhesive face may lower the adhesion between the backing sheet and the pressure-sensitive adhesive sheet when the two sheets after removal from each other are laminated again on each other. The configuration, where the identification sheet X1 bears or includes an engraved mark formed by laser marking as at least one of the distinguishing mark M1 and the distinguishing mark M2, is advantageous for avoiding or minimizing the deformation or unevenness at the adhesive face 22a in the pressure-sensitive adhesive sheet 20 and for surely providing adhesion between the backing sheet 10 and the pressure-sensitive adhesive sheet 20 after the two sheets are laminated again on each other.

In possible configurations of the identification sheet X1 as above, two or more identification sheets X1 may be arrayed and unified, as illustrated in FIG. 4. FIG. 4 illustrates a configuration in which six identification sheets X1 are arrayed and unified. In the configuration as above, distinguishing marks M1 are made individually in boxes at the outer face 10a. The distinguishing marks M1 have pattern shapes different from one another. At the outer face 20a (not shown), distinguishing marks M2 (not shown) are made respectively corresponding to the distinguishing marks M1 at the outer face 10a. The distinguishing marks M2 at the outer face 20a also have pattern shapes different from one another. The pairs of distinguishing marks M1 and M2, which function as pairs of cross-check information, are present in individual boxes. The identification sheet including identification sheets X1 being arrayed and unified may be cut into pieces having a necessary size before use. As described above, in a possible configuration of the identification sheet X1, two or more identification sheets X1 are arrayed and unified. Such a configuration is also applicable to an identification sheet according to an embodiment described below.

FIG. 5 is a partial enlarged cross-sectional view of an identification sheet X2 according to one embodiment of the present invention. The identification sheet X2 includes a backing sheet 10 and a pressure-sensitive adhesive sheet 20, which are removable from each other. The backing sheet 10 has a multilayer structure including a base layer 11, a writable layer 12, a background layer 13, and a release layer 14. The pressure-sensitive adhesive sheet 20 has a multilayer structure including a substrate layer 21 and a pressure-sensitive adhesive layer 22. The identification sheet X2 has an outer face 10a and an outer face 20a. The outer face 10a can serve as an outer surface defined by the backing sheet 10; whereas the outer face 20a can serve as an outer surface defined by the pressure-sensitive adhesive sheet 20. The outer face 10a defined by the backing sheet 10 bears a distinguishing mark M3 which carries distinguishing information. The outer face 20a defined by the pressure-sensitive adhesive sheet 20 bears a distinguishing mark M4 which carries distinguishing information. The identification sheet X2 as above is different from the identification sheet X1 in having the distinguishing mark M3 instead of the distinguishing mark M1, and having the distinguishing mark M4 instead of the distinguishing mark M2. The identification sheet X2 has configurations similar to those of the identification sheet X1, except for configurations relating to the distinguishing marks M3 and M4.

The distinguishing marks M3 and M4 are independently printed marks. As used herein, the term "printed mark" refers to a mark which is formed by a printing technique on a face to be marked. Non-limiting examples of the printing technique include inkjet printing, thermal transfer printing, gravure printing, relief printing, silk-screen printing, stamp printing, and printing using a baking process. The distinguishing marks M3 and M4 may each independently be formed by printing with an ink having a large contrast difference from a corresponding background color, or with an ink having a small contrast difference from the corresponding background color. Alternatively, the distinguishing marks M3 and M4 may each independently be formed by printing typically with an ink that develops a color upon ultraviolet irradiation.

These distinguishing marks M3 and M4 are designed to correspond to each other, so as to function as a pair of cross-check information for determining whether a backing sheet 10 with the distinguishing mark M3 and a pressure-sensitive adhesive sheet 20 with the distinguishing mark M4 correspond to each other. Specifically, the distinguishing marks M3 and M4 may have pattern shapes identical to each other and function as a pair of cross-check information; or may have pattern shapes different from each other and function as a pair of cross-check information. In another embodiment, the identification sheet X2 is designed to have a partial region that is transparent all over the thickness direction of the sheet X2. In this embodiment, the distinguishing mark M3 is disposed in the partial region in the outer face 10a; the distinguishing mark M4 is disposed in the partial region in the outer face 20a; and these distinguishing marks M3 and M4 can be seen at one time from the outer face 10a side or from the outer face 20a side and function as a pair of cross-check information. Elementary shapes which may be included in the pattern shapes of the distinguishing marks M3 and M4 are, for example, as with the elementary shapes which may be included in the pattern shapes of the distinguishing marks M1 and M2 in the identification sheet X1.

The identification sheet X2, which has the configurations as above, may be produced typically by a procedure as with the production process for the identification sheet X1, except for forming printed marks, instead of the engraved marks, at the outer faces 10a and 20a. The identification sheet X2 may be used by a procedure similar to that for the identification sheet X1 as described above.

In the identification sheet X2, the distinguishing mark M3 at the backing sheet 10 and the distinguishing mark M4 at the pressure-sensitive adhesive sheet 20, where the two marks correspond to each other, form a pair in the single identification sheet. This certifies that the backing sheet 10 and the pressure-sensitive adhesive sheet 20 correspond to each other. This is advantageous for restraining a tampering act and mistaking of the sheet(s) for another one in the identification sheet, as with that the pairing (correspondence) of the distinguishing marks M1 and M2 in the identification sheet X1 certifies that the backing sheet 10 and the pressure-sensitive adhesive sheet 20 correspond to each other. In the identification sheet X2, the distinguishing mark M3 has been formed at the outer face 10a of the backing sheet 10, separately from the distinguishing mark M4; and the distinguishing mark M4 has been formed at the outer face 20a of the pressure-sensitive adhesive sheet 20, separately from the distinguishing mark M3. The distinguishing marks M3 and M4 are each neither one formed by copying as a result of a transferring action of a coloring component constituting part of another distinguishing mark; nor one formed by copying as a result of a physical and/or chemical reaction caused typically by local heating, pressurization, or photoirradiation in the formation of another distinguishing mark. This configuration is advantageous for restraining or avoiding the deterioration of the distinguishing marks M3 and M4. The configuration is therefore advantageous for allowing the distinguishing marks M3 and M4 to keep on functioning as a pair of cross-check information to determine whether a backing sheet 10 with the distinguishing mark M3 and a pressure-sensitive adhesive sheet 20 with the distinguishing mark M4 correspond to each other.

As described above, the identification sheet X2 is suitable for restraining a tampering act on the identification sheet after the collection of the target material and for restraining the mistaking of the pressure-sensitive adhesive sheet 20 or the backing sheet 10 for another one during a collecting process and an identifying operation for the target material. Consequently, the identification sheet X2 is suitable for keeping on surely providing the admissibility of evidence of the collected target material, where the admissibility of evidence is required typically in a criminal case.

In the identification sheet X2, the distinguishing mark M1 described above relating to the identification sheet X1 may be made, instead of the distinguishing mark M3, at the outer face 10a defined by the backing sheet 10. Also in the identification sheet X2, the distinguishing mark M2 described above relating to the identification sheet X1 may be disposed at the outer face 20a defined by the pressure-sensitive adhesive sheet 20, instead of the distinguishing mark M4.

EXAMPLES

Example 1

Preparation of Urethane Pressure-Sensitive Adhesive Solution

Material components were placed in a flask equipped with a reflux condenser, a nitrogen gas inlet tube, a stirrer, and a thermometer. The components were 0.096 mol of adipic acid (supplied by Wako Pure Chemical Industries, Ltd.), 0.127 mol of neopentyl glycol (supplied by Wako Pure Chemical Industries, Ltd.), 0.071 mol of a polypropylene glycol having a number average molecular weight of 1000 (supplied by Wako Pure Chemical Industries, Ltd.), and, as a solvent, 100 g of decahydronaphthalene (supplied by Wako Pure Chemical Industries, Ltd.). With introduction of nitrogen gas into the flask, the components in the flask were stirred at a temperature maintained in the range of 180° C. to 200° C. for 12 hours (dehydrative condensation). Next, the solvent was distilled off from the reaction solution in the flask to leave a residue, and the residue was combined with 100 g of tetrahydrofuran as a solvent. Next, after changing the temperature to 90° C., the solution in the flask was combined with 0.064 mol of hexamethylene diisocyanate (supplied by Wako Pure Chemical Industries, Ltd.) and 0.001 mol of dibutyltin dilaurate (supplied by Wako Pure Chemical Industries, Ltd.) as a urethane synthesis catalyst. The resulting solution in the flask was stirred for 15 hours with introduction of nitrogen gas into the flask (polyurethanization). Next, the solvent was distilled off from the reaction solution to leave a solid, and the solid was mixed with toluene to yield a pressure-sensitive adhesive solution (pressure-sensitive adhesive solution S1) containing a polyester polyurethane, which serves as a pressure-sensitive adhesive. The pressure-sensitive adhesive solution S1 had a solids concentration of 55 mass percent.

Production of Identification Sheet

The pressure-sensitive adhesive solution S1 was applied onto a 75-μm thick transparent polyethylene terephthalate film LUMIRROR T60 (trade name, supplied by Toray Industries Inc.) to constitute a substrate layer of a transparent pressure-sensitive adhesive sheet, and the applied solution was dried to form a 280-μm thick transparent pressure-sensitive adhesive layer. Thus, a transparent pressure-sensitive adhesive sheet for an identification sheet according to this example was prepared. Next, the transparent pressure-sensitive adhesive sheet was laminated at its pressure-sensitive adhesive layer or adhesive face onto a mount face of a backing sheet. The backing sheet had a multilayer structure including a base layer, a writable layer, a background layer, and a release layer. The base layer included a synthetic paper YUPO FPG (trade name, 130 μm, supplied by YUPO CORPORATION). The writable layer was formed by the application of a lamination ink LAMIOL MARK III (trade name, supplied by SAKATA INX CORPORATION) and provided a writable surface. The background layer was formed by solid printing (wide area printing) of a white ink Lamic F220 (trade name, supplied by Dainichiseika Color & Chemicals Mfg. Co., Ltd.). The release layer was made of a 60-μm thick transparent OPP film (biaxially stretched polypropylene film) and defined the mount face of the backing sheet. In the resulting sheet laminate (including the backing sheet and the transparent pressure-sensitive adhesive sheet), the outer surface of the backing sheet defined by the writable layer constitutes a first outer face; and the outer surface of the transparent pressure-sensitive adhesive sheet defined by the substrate layer constitutes a second outer face.

Next, distinguishing marks were formed separately at the first outer face and at the second outer face of the sheet laminate. Specifically, a series of numeric characters "1243567890" as a first distinguishing mark was formed at the first outer face by laser marking, and, separately, a series of numeric characters "1243567890" as a second distinguishing mark was formed at the second outer face by laser marking, using a $CO_2$ laser marker LP-420 (trade name, supplied by Panasonic Industrial Devices SUNX Co., Ltd.). The laser marking was performed with an output of the laser marker of 50% at a scanning speed of 500 mm/second. The laser marking could be performed without coloring individually at the first outer face and at the second outer face.

The identification sheet according to Example 1 could be produced by the above procedure. This identification sheet had a laser mark, which functions as one of a pair of cross-check information, at the outer surface defined by the backing sheet, and another laser mark, which functions as the other of the pair of cross-check information, at the outer surface defined by the transparent pressure-sensitive adhesive sheet.

Example 2

An identification sheet according to Example 2 was produced by a procedure similar to that for the identification sheet according to Example 1, except for employing a 60-μm thick transparent polyethylene film NSO Film (trade name, supplied by Okura Industrial Co., Ltd.) as a substrate layer of the transparent pressure-sensitive adhesive sheet, instead of the 75-μm thick transparent polyethylene terephthalate film. Laser marking and a series of numeric characters were employed respectively as the marking technique and the distinguishing marks to be formed in this example, as with Example 1. Also in this example, the laser marking could be performed without coloring individually at the first outer face and at the second outer face.

Example 3

An identification sheet according to Example 3 was produced by a procedure similar to that for the identification sheet according to Example 1, except for employing a 25-μm thick transparent polyethylene terephthalate film LUMIRROR T60 (trade name, supplied by Toray Industries Inc.) as a substrate layer of the transparent pressure-sensitive adhesive sheet, instead of the 75-μm thick transparent polyethylene terephthalate film. Laser marking and a series of numeric characters were employed respectively as the marking technique and the distinguishing marks to be formed in this example, as with Example 1. Also in this example, the laser marking could be performed without coloring individually at the first outer face and at the second outer face.

Example 4

An identification sheet according to Example 4 was produced by a procedure similar to that for the identification sheet according to Example 1, except for employing a 188-μm thick a transparent polyethylene terephthalate film LUMIRROR T60 (trade name, supplied by Toray Industries Inc.) as a substrate layer of the transparent pressure-sensitive adhesive sheet, instead of the 75-μm thick transparent polyethylene terephthalate film. Laser marking and a series of numeric characters were employed respectively as the marking technique and the distinguishing marks to be formed in this example, as with Example 1. Also in this example, the laser marking could be performed without coloring individually at the first outer face and at the second outer face.

Example 5

Preparation of Acrylic Pressure-Sensitive Adhesive Solution

Material components were placed in a flask equipped with a reflux condenser, a nitrogen gas inlet tube, a stirrer, and a thermometer. The components were 100 parts by mass of 2-ethylhexyl acrylate (2EHA), 4 parts by mass of 2-hydroxyethyl acrylate (HEA), and 30 parts by mass of ethyl acetate as a polymerization solvent. The components in the flask were stirred at 23° C. to 27° C. for 6 hours with introduction of nitrogen gas into the flask to thereby remove oxygen from the reaction system. Next, the components in the flask were combined with 0.2 part by mass of 2,2'-azobisisobutyronitrile (AIBN), heated up to 80° C., and subjected to a polymerization reaction for 12 hours. This gave a solution containing an acrylic polymer. The resulting acrylic polymer solution was combined with, per 100 parts by mass of the acrylic polymer, 1 part by mass of an aromatic polyisocyanate CORONATE HL (trade name, supplied by Nippon Polyurethane Industry Co., Ltd.) as a crosslinker. The resulting solution mixture was diluted with ethyl acetate to have a solids concentration of 30 mass percent. This yielded a pressure-sensitive adhesive solution (pressure-sensitive adhesive solution S2) containing the acrylic polymer, which serves as a pressure-sensitive adhesive.

Production of Identification Sheet

A sheet laminate (including a backing sheet and a transparent pressure-sensitive adhesive sheet) was prepared by a procedure similar to that in Example 1, except for using the pressure-sensitive adhesive solution S2 containing the acrylic polymer, instead of the pressure-sensitive adhesive solution S1 containing the polyester polyurethane, to form a pressure-sensitive adhesive layer of the transparent pressure-sensitive adhesive sheet. Distinguishing marks were formed individually at the first outer face defined by backing sheet and at the second outer face defined by the transparent pressure-sensitive adhesive sheet in the sheet laminate, by a procedure similar to that in Example 1. Laser marking and a series of numeric characters were employed respectively as the marking technique and the distinguishing marks to be formed in this example, as with Example 1. Also in this example, the laser marking could be performed without coloring individually at the first outer face and at the second outer face. Thus, an identification sheet according to Example 5 could be produced. This identification sheet had a laser mark, which functions as one of a pair of cross-check information, at the outer surface defined by the backing sheet, and another laser mark, which functions as the other of the pair of cross-check information, at the outer surface defined by the transparent pressure-sensitive adhesive sheet.

Example 6

Preparation of Urethane Pressure-Sensitive Adhesive Solution

Material components were placed in a flask equipped with a reflux condenser, a nitrogen gas inlet tube, a stirrer, and a thermometer. The components were 0.07 mol of a polypropylene glycol having a number average molecular weight of 2000 (supplied by Wako Pure Chemical Industries, Ltd.), 0.064 mol of hexamethylene diisocyanate (supplied by Wako Pure Chemical Industries, Ltd.), 0.001 mol of dibutyltin dilaurate (supplied by Wako Pure Chemical Industries, Ltd.) as a urethane synthesis catalyst, and 100 g of tetrahydrofuran (supplied by Wako Pure Chemical Industries, Ltd.) as a solvent. The components placed in the flask were stirred at 90° C. for 15 hours with introduction of nitrogen gas into the flask (polyurethanization). Next, the solvent was distilled off from the reaction solution to leave a solid, and the solid was mixed with ethyl acetate and yielded a pressure-sensitive adhesive solution (pressure-sensitive adhesive solution S3). This contained a polyether polyurethane, which serves as a pressure-sensitive adhesive. The pressure-sensitive adhesive solution S3 had a solids concentration of 55 mass percent.

Production of Identification Sheet

A sheet laminate (including a backing sheet and a transparent pressure-sensitive adhesive sheet) was prepared by a procedure similar to that in Example 1, except for using the pressure-sensitive adhesive solution S3 containing the polyether polyurethane, instead of the pressure-sensitive adhesive solution S1 containing the polyester polyurethane, to form a pressure-sensitive adhesive layer of the transparent pressure-sensitive adhesive sheet. In the sheet laminate, distinguishing marks were formed individually at the first outer face defined by the backing sheet and at the second outer face defined by the transparent pressure-sensitive adhesive sheet, by a procedure similar to that in Example 1. Laser marking and a series of numeric characters were employed respectively as the marking technique and the distinguishing marks to be formed in this example, as with Example 1. Also in this example, the laser marking could be performed without coloring individually at the first outer face and at the second outer face. Thus, an identification sheet according to Example 6 could be produced. This identification sheet had a laser mark, which functions as one of a pair of cross-check information, at the outer surface defined by the backing sheet, and another laser mark, which functions as the other of the pair of cross-check information, at the outer surface defined by the transparent pressure-sensitive adhesive sheet.

Example 7

An identification sheet according to Example 7 was produced through a process similar to that for the identification sheet according to Example 1, except for employing marking by printing, instead of the laser marking, to mark distinguishing marks. In the example, the distinguishing marks were made individually at the first outer face and at the second outer face of the sheet laminate described above in Example 1, by relief printing using an UV-curable ink. Specifically, a first bar code (one-dimensional bar code) as a first distinguishing mark was formed at the first outer face by printing, and a second bar code (one-dimensional bar code identical to the first bar code) as a second distinguishing mark was formed at the second outer face by printing, using a UV printing machine (supplied by Iwasaki Tekko Co., Ltd.). The marking by relief printing was performed at a UV output of the printing machine of 1.5 kV using, as a printing ink, a white UV ink UV 161 (trade name, supplied by T&K TOKA CO., LTD.). Thus, an identification sheet according to Example 7 could be produced. This identification sheet had a printed mark (bar code), which functions as one of a pair of cross-check information, at the outer surface defined by the backing sheet, and another printed mark (bar code), which functions as the other of the pair of cross-check information, at the outer surface defined by the transparent pressure-sensitive adhesive sheet.

Example 8

An identification sheet according to Example 8 was produced through a process similar to that in Example 1, except for employing marking by printing, instead of the laser marking, to mark (to form) distinguishing marks. In this example, the distinguishing marks were made by thermal transfer printing individually at the first outer face and at the second outer face of the sheet laminate. Specifically, a first QR Code as a first distinguishing mark was made by printing at the first outer face, and a second QR Code (identical to the first QR Code) as a second distinguishing mark was made by printing at the second outer face, using a thermal printer DURAPRINTER SI600 (trade name, supplied by Nitto Denko Corporation). This marking by thermal transfer printing was performed using a black thermal transfer ink DURAINK H20 (trade name, supplied by Nitto Denko Corporation) as a printing ink. Thus, an identification sheet according to Example 8 could be produced. This identification sheet had a printed mark (QR Code), which functions as one of a pair of cross-check information, at the outer surface defined by the backing sheet, and another printed mark (QR Code), which functions as the other of the pair of cross-check information, at the outer surface defined by the transparent pressure-sensitive adhesive sheet.

As a summary of the above description, the configurations according to the present invention and variations or modifications thereof will be listed below as appendices.

Appendix 1

An identification sheet including:
a backing sheet bearing a first distinguishing mark; and
a pressure-sensitive adhesive sheet bearing a second distinguishing mark, the pressure-sensitive adhesive sheet having a multilayer structure including:
a pressure-sensitive adhesive layer being removably attachable to the backing sheet; and
a substrate layer.

Appendix 2

An identification sheet including:
a backing sheet having a first outer face bearing a first distinguishing mark, and a mount face on opposite side to the first outer face; and
a pressure-sensitive adhesive sheet having a multilayer structure including:
a pressure-sensitive adhesive layer being removably attachable to the mount face of the backing sheet; and
a substrate layer,
the pressure-sensitive adhesive sheet having a second outer face bearing a second distinguishing mark, the second outer face being disposed in the substrate layer on opposite side to the pressure-sensitive adhesive layer.

Appendix 3

The identification sheet according to one of Appendices 1 and 2, wherein the first distinguishing mark and the second distinguishing mark are each independently selected from an engraved mark and a printed mark.

Appendix 4

The identification sheet according to Appendix 3, wherein the engraved mark is selected from a mark resulting from laser marking, and a mark resulting from air pen marking.

Appendix 5

The identification sheet according to any one of Appendices 1 to 4, wherein the first distinguishing mark and the second distinguishing mark have pattern shapes identical to each other.

Appendix 6

The identification sheet according to any one of Appendices 1 to 4, wherein the first distinguishing mark and the second distinguishing mark have pattern shapes different from each other.

Appendix 7

The identification sheet according to any one of Appendices 1 to 6, wherein the first distinguishing mark and the second distinguishing mark each independently include at least one selected from the group consisting of numeric characters, alphabetic characters, hiragana characters, katakana characters, kanji characters, symbols, bar codes, and QR Codes.

Appendix 8

The identification sheet according to any one of Appendices 1 to 7, wherein the backing sheet has a writable surface.

Appendix 9

The identification sheet according to any one of Appendices 1 to 8,
wherein the substrate layer includes one of a polyethylene terephthalate film and a polyolefin film.

Appendix 10

The identification sheet according to any one of Appendices 1 to 9, wherein the substrate layer has a thickness of 2.5 to 500 µm.

Appendix 11

The identification sheet according to any one of Appendices 1 to 10,
which is used for collecting a target material to be identified.

Appendix 12

The identification sheet according to any one of Appendices 1 to 11, wherein the pressure-sensitive adhesive layer includes a polyurethane as a principal component.

Appendix 13

The identification sheet according to Appendix 12, wherein the polyurethane has a softening temperature of 190° C. to 280° C.

Appendix 14

The identification sheet according to one of Appendices 12 and 13, wherein the polyurethane is a polyester polyurethane.

Appendix 15

The identification sheet according to Appendix 14, wherein the polyester polyurethane is a polyester-polyether polyurethane.

Appendix 16

The identification sheet according to any one of Appendices 1 to 11, wherein the pressure-sensitive adhesive layer includes an acrylic polymer as a principal component.

Appendix 17

The identification sheet according to one of Appendices 14 and 15,
wherein the polyester polyurethane includes units derived from a multifunctional isocyanate, units derived from a polycarboxylic acid, and units derived from a first polyhydric alcohol.

Appendix 18

The identification sheet according to Appendix 15, wherein the polyester-polyether polyurethane includes units derived from a multifunctional isocyanate, units derived from a polycarboxylic acid, units derived from a first polyhydric alcohol, and units derived from a second polyhydric alcohol containing an ether bond.

Appendix 19

The identification sheet according to Appendix 18, wherein, in the polyester-polyether polyurethane, the ratio of the total number of hydroxy groups in the first polyhydric alcohol to the total number of hydroxy groups in the second polyhydric alcohol is 1.5 to 9.0.

Appendix 20

The identification sheet according to one of Appendices 18 and 19, wherein the second polyhydric alcohol to form the polyester-polyether polyurethane is a multimer that is a polymer derived from a single type of monomer, and wherein, in the polyester-polyether polyurethane, the ratio of the total number of hydroxy groups in the first polyhydric alcohol to the total number of units derived from the single type of monomer in the second polyhydric alcohol is 0.1 to 0.4.

Appendix 21

The identification sheet according to any one of Appendices 18 to 20, wherein the second polyhydric alcohol is an aliphatic or alicyclic polyhydric alcohol containing an ether bond.

Appendix 22

The identification sheet according to Appendix 21, wherein the second polyhydric alcohol is a polypropylene glycol.

Appendix 23

The identification sheet according to any one of Appendices 17 to 22, wherein, in the polyester polyurethane, the ratio of the total number of hydroxy groups in the polyhydric alcohol(s) to the sum of the total number of isocyanate groups in the multifunctional isocyanate and the total number of carboxy groups in the polycarboxylic acid is 0.5 to 1.5.

Appendix 24

The identification sheet according to any one of Appendices 17 to 23, wherein, in the polyester polyurethane, the ratio of the total number of isocyanate groups in the multifunctional isocyanate to the total number of carboxy groups in the polycarboxylic acid is 0.5 to 1.0.

Appendix 25

The identification sheet according to any one of Appendices 17 to 24, wherein the multifunctional isocyanate is an aliphatic or alicyclic multifunctional isocyanate.

Appendix 26

The identification sheet according to Appendix 25, wherein the multifunctional isocyanate is at least one selected from the group consisting of hexamethylene diisocyanate, 1,3-bis(isocyanatomethyl)cyclohexane, isophorone diisocyanate, 4,4'-methylenebis(cyclohexyl isocyanate), and hydrogenated diphenylmethane diisocyanate.

Appendix 27

The identification sheet according to any one of Appendices 17 to 26, wherein the polycarboxylic acid is an aliphatic or alicyclic polycarboxylic acid.

Appendix 28

The identification sheet according to Appendix 27, wherein the polycarboxylic acid is adipic acid.

Appendix 29

The identification sheet according to any one of Appendices 17 to 28, wherein the first polyhydric alcohol is an aliphatic or alicyclic polyhydric alcohol.

Appendix 30

The identification sheet according to Appendix 29, wherein the first polyhydric alcohol is neopentyl glycol.

REFERENCE SIGNS LIST

X1, X2 identification sheet
M1, M2, M3, M4 distinguishing mark
10 backing sheet
10a outer face
10b mount face
11 base layer
12 writable layer
13 background layer
14 release layer
20 pressure-sensitive adhesive sheet
20a outer face
21 substrate layer
22 pressure-sensitive adhesive layer
22a adhesive face

The invention claimed is:

1. An identification sheet comprising:
    a backing sheet bearing a first distinguishing mark; and
    a pressure-sensitive adhesive sheet bearing a second distinguishing mark,
    the pressure-sensitive adhesive sheet having a multilayer structure comprising:
        a pressure-sensitive adhesive layer being removably attachable to the backing sheet; and
        a substrate layer,
    wherein the pressure-sensitive adhesive layer comprises a polyurethane or an acrylic polymer as a principal component.

2. The identification sheet according to claim 1, wherein the first distinguishing mark and the second distinguishing mark are each independently selected from an engraved mark and a printed mark.

3. The identification sheet according to claim 2,
    wherein the engraved mark is selected from:
    a mark resulting from laser marking; and
    a mark resulting from air pen marking,
        wherein the laser marking is performed by a $CO_2$ laser, a UV laser, a green laser, or a fiber laser.

4. The identification sheet according to claim 1, wherein the first distinguishing mark and the second distinguishing mark have pattern shapes identical to each other.

5. The identification sheet according to claim 1, wherein the first distinguishing mark and the second distinguishing mark have pattern shapes different from each other.

6. The identification sheet according to claim 1, wherein the first distinguishing mark and the second distinguishing mark each independently include at least one selected from the group consisting of:
    numeric characters;
    alphabetic characters;
    hiragana characters;
    katakana characters;
    kanji characters;
    symbols;
    bar codes; and
    QR Codes.

7. The identification sheet according to claim 1, wherein the backing sheet has a writable surface.

8. The identification sheet according to claim 1, wherein the substrate layer comprises one of a polyethylene terephthalate film and a polyolefin film.

9. The identification sheet according to claim 1, wherein the substrate layer has a thickness of 2.5 to 500 μm.

10. The identification sheet according to claim 1, which is for use in collection of a target material to be identified.

11. The identification sheet according to claim 1,
    wherein the polyurethane has a softening temperature of 190° C. to 280° C.

12. The identification sheet according to claim 1, wherein the polyurethane is a polyester polyurethane.

13. The identification sheet according to claim 12,
    wherein the polyester polyurethane is a polyester-polyether polyurethane.

14. The identification sheet according to claim 1, wherein the backing sheet has a multilayer structure including a base layer and a writable layer having a writable surface.

* * * * *